US012740757B1

(12) United States Patent
Barve et al.

(10) Patent No.: US 12,740,757 B1
(45) Date of Patent: Sep. 22, 2026

(54) SYSTEM AND METHOD FOR SWEEP TRAJECTORY SIMULATION

(71) Applicant: Anumana, Inc., Cambridge, MA (US)

(72) Inventors: Rakesh Barve, Bengaluru (IN); Murali Aravamudan, Andover, MA (US)

(73) Assignee: Anumana, Inc., Cambridge, MA (US)

(*) Notice: Subject to any disclaimer, the term of this patent is extended or adjusted under 35 U.S.C. 154(b) by 0 days.

(21) Appl. No.: 19/188,841

(22) Filed: Apr. 24, 2025

(51) Int. Cl.
*A61B 8/08* (2006.01)
*A61B 8/00* (2006.01)
*A61B 8/12* (2006.01)
*G06T 17/00* (2006.01)

(52) U.S. Cl.
CPC .............. *A61B 8/0883* (2013.01); *A61B 8/12* (2013.01); *A61B 8/4245* (2013.01); *A61B 8/52* (2013.01); *G06T 17/00* (2013.01)

(58) Field of Classification Search
None
See application file for complete search history.

(56) References Cited

U.S. PATENT DOCUMENTS

2008/0020362 A1* 1/2008 Cotin .................. G09B 23/285 434/267
2017/0110032 A1 4/2017 O'Brien et al.
2019/0385061 A1* 12/2019 Chaudhury .............. G06N 7/01
2023/0363821 A1 11/2023 Levin et al.
2024/0303501 A1 9/2024 Zhang et al.
2024/0307123 A1* 9/2024 Schegg .................. A61B 34/30
2025/0049516 A1* 2/2025 Fotouhi .................. A61B 34/10
2025/0099717 A1* 3/2025 Collins .................. A61B 34/10

FOREIGN PATENT DOCUMENTS

EP 4197476 A1 6/2023
WO 2017036027 A1 3/2017
WO 2022254436 A1 12/2022

OTHER PUBLICATIONS

Yuan Bi et al; VesNet-RL: Simulation-based Reinforcement Learning for Real-World US Probe Navigation; IEEE Robotics and Automation Letters. Preprint Version. Accepted Apr. 2022.
A A Amadou et al; Cardiac ultrasound simulation for autonomous ultrasound navigation; Front Cardiovasc Med. Aug. 13, 2024.
Yuan Bi et al; Autonomous Path Planning for Intercostal Robotic Ultrasound Imaging Using Reinforcement Learning "License: arXiv. org perpetual non-exclusive licensearXiv:2404.09927v1 [cs.RO] Apr. 15, 2024".

* cited by examiner

*Primary Examiner* — Shahdeep Mohammed
(74) *Attorney, Agent, or Firm* — CALDWELL LLC

(57) ABSTRACT

A system for sweep trajectory simulation, wherein the system includes at least a processor and a memory communicatively connected to the at least a processor, wherein the memory contains instructions configuring the at least a processor to receive a plurality of 3D imaging data, generate, using the plurality of 3D imaging data, ultrasound simulation data, wherein the ultrasound simulation data includes ultrasound data and probe position data, generate, using the ultrasound simulation data, a plurality of 3D models, and train, using reinforcement learning algorithms, a sweep trajectory simulation model. In an embodiment, the sweep trajectory simulation model is trained using 3D imaging data, the probe position data, and the plurality of 3D models and the sweep trajectory simulation model is configured to output a time-step vector relating to the movement of a catheter.

20 Claims, 12 Drawing Sheets

1200
Display
1236
Display Adaptor
1252
Input Device
1232
Storage Device
Medium
Instructions
1224
1228
1220
1212
1116
Network Interface
1240
Instructions
1220
Input/ Output System
1208
Peripheral Interface(s)
1256
Instructions
Processors
1220
1204
Network
1244
Remote Device
1248

SYSTEM AND METHOD FOR SWEEP TRAJECTORY SIMULATION

FIELD OF THE INVENTION

The present invention generally relates to the field of simulations. In particular, the present invention is directed to systems and methods for sweep trajectory simulation.

BACKGROUND

Sweep trajectories in ultrasonic procedures of the heart refer to the pattern in which an ultrasound probe moves or "sweeps" across the heart to capture detailed images or Doppler signals. These procedures are commonly used in echocardiography to assess heart function, including the motion of heart valves, blood flow, and myocardial performance. By employing specific trajectories, such as sector sweeps or linear scans, clinicians can obtain a comprehensive view of the heart from various angles and depths. This technique enhances the ability to detect abnormalities like valve dysfunction, thrombi, or cardiac chamber enlargement. The use of precise sweep trajectories is crucial for accurate diagnostics and guiding interventions.

SUMMARY OF THE DISCLOSURE

In an aspect, a system for sweep trajectory simulation may include at least a processor and a memory communicatively connected to the at least a processor, wherein the memory contains instructions configuring the at least a processor to receive a plurality of 3D imaging data, generate, using the plurality of 3D imaging data, ultrasound simulation data, wherein the ultrasound simulation data includes ultrasound data and probe position data, generate, using the ultrasound simulation data, a plurality of 3D models, and train, using reinforcement learning algorithms, a sweep trajectory simulation model. In an embodiment, the sweep trajectory simulation model is trained using 3D imaging data, the probe position data, and the plurality of 3D models and the sweep trajectory simulation model is configured to output a time-step vector relating to the movement of a catheter.

In another aspect, a method for sweep trajectory simulation may include to receiving a plurality of 3D imaging data, generating, using the plurality of 3D imaging data, ultrasound simulation data, wherein the ultrasound simulation data includes ultrasound data and probe position data, generate, using the ultrasound simulation data, a plurality of 3D models, and training, using reinforcement learning algorithms, a sweep trajectory simulation model. In an embodiment, the sweep trajectory simulation model is trained using 3D imaging data, the probe position data, and the plurality of 3D models and the sweep trajectory simulation model is configured to output a time-step vector relating to the movement of a catheter.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for sweep trajectory simulation. In an embodiment, the present disclosure may train a sweep trajectory simulation model which may be used to optimize sweep trajectories and procedure planning.

Aspects of the present disclosure can be used to train the model to learn optimal trajectories in order to avoid potential obstacles such as blood vessel walls or other tissues that may impact the success of the procedure. Aspects of the present disclosure can also be used to train the sweep trajectory simulation model to learn optimal sweep trajectories that yield accurate 3D models. In some embodiments, the trajectories may be optimized as a function of a number of sweeps. This is so, at least in part, because the sweep trajectory simulation model may be trained using reinforcement learning, which provides a framework to generate additional training data.

Aspects of the present disclosure allow for sweep trajectory simulation. Exemplary embodiments illustrating aspects of the present disclosure are described below in the context of several specific examples.

Figure 1:
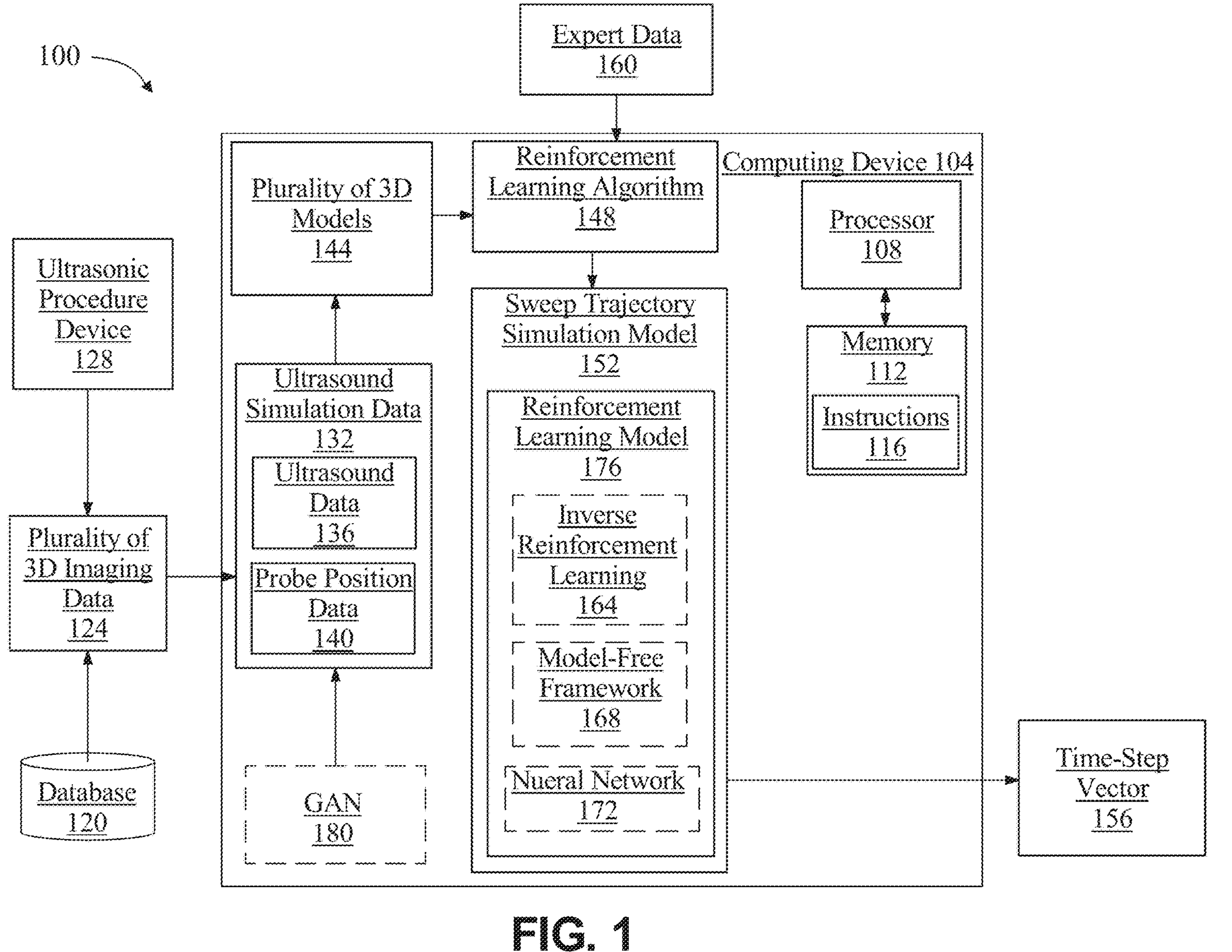
FIG. 1 is block diagram of an exemplary embodiment of a system for sweep trajectory simulation.

Referring now to FIG. 1, an exemplary embodiment of a system 100 for sweep trajectory simulation is illustrated. System 100 may include at least a processor 108 and a memory 112 communicatively connected to the at least a processor 108, wherein the memory 112 contains instructions 116 configuring the at least a processor 108 to receive a plurality of 3D imaging data 124, generate, using the plurality of 3D imaging data 124, ultrasound simulation data

132, wherein the ultrasound simulation data 132 includes ultrasound data 136 and probe position data 140, generate, using the ultrasound simulation data 132, a plurality of 3D models 144, and train, using reinforcement learning algorithms 148, a sweep trajectory simulation model 152. In an embodiment, the sweep trajectory simulation model 152 is trained using 3D imaging data, the probe position data 140, and the plurality of 3D models 144 and the sweep trajectory simulation model 152 is configured to output a time-step vector 156 relating to the movement of a catheter.

In continued reference to FIG. 1, system 100 includes a computing device 104. Computing device 104 includes a processor communicatively connected to a memory 112. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

In further reference to FIG. 1, in an embodiment, at least a processor 108 is configured to receive a plurality of 3D imaging data 124. 3D imaging data may include data from an imaging device. For example, imaging devices may include computed tomography (CT), magnetic resonance imaging (M RI), and/or ultrasound. As used throughout this disclosure, "3D imaging" refers to the process of creating three-dimensional representations of objects or environments, using specialized imaging techniques. In an embodiment, 3D imaging may combine multiple 2D images and/or scans, such as those from CT, MRI, and/or ultrasound, to reconstruct a 3D model of the area of interest. In an embodiment, 3D imaging data may include both 2D and 3D imaging data. The 2D imaging data may be transformed into 3D data by stitching the 2D imaging data together to make a 3D model. In an embodiment, 3D imaging data may include spatial information, volume data, surface models, textural information, functional data, annotations and measurements, and/or the like. For example, 3D imaging data may include point clouds, meshes, textures and materials, voxel data, and/or other associated data.

Still referring to FIG. 1, a "point cloud," as used herein, is a collection of data points in a three-dimensional space. In an embodiment, a point cloud may be captured using 3D scanning technologies. Each point in a point cloud may represent a specific location in space, which may include spatial coordinates (x, y, z), and in some cases, additionally data such as color and/or intensity. Point clouds may be used to represent the external surface of objects and/or environments in 3D. In an embodiment, point clouds may serve as foundational data for creating 3D models 144. In an embodiment, point clouds may be generated from CT and/or M RI scans to create detailed anatomical models for diagnosis, treatment planning, and visualization. As used throughout this disclosure, a "mesh" is a collection of vertices, edges, and faces that define the shape of a 3D object in space. In an embodiment, the vertices are points in 3D space, the edges are straight lines connecting pairs of vertices, and the faces are flat surfaces enclosed by edges. In an embodiment, meshes may be derived from point clouds, and/or volumetric data.

With continued reference to FIG. 1, "textures and materials," as used herein refer to the visual properties applied to the surface of a 3D model. Textures and materials may enhance the realism of a model and/or convey specific characteristics. In an embodiment, textures may include 2D images and/or maps that are applied to the surface of a 3D model to simulate details such as color, patterns, and/or surface features. In some cases, textures may be mapped onto a model's surface using UV coordinates, allowing them to wrap around the shape. Materials may define how a surface interacts with light, influencing a model's appearance in terms of reflectivity, glossiness, transparency, and/or how it reacts to different lighting conditions. Materials may include properties such as diffuse color, specularity, and/or bump maps. In an embodiment, materials may help simulate tissue properties, such as the soft tissue of muscles and/or the hard surface of bone and enhance the understanding of structures in 3D models 144.

In further reference to FIG. 1, as used herein, "voxel data," refers to three-dimensional pixels, or voxels, that represent values in a 3D grid. In an embodiment, each voxel may correspond to a small cube or box within the volume and may contain information about a specific point in space, such as tissue, density, color, and/or other attributes depending on the imaging modality. Voxel data may be used in medical imaging, such as CT, M RI and/or positron emission tomography (PET) scans, to create volumetric images of the body. Unlike 2D images, where each pixel corresponds to a point in two-dimensional space, voxels provide detailed 3D spatial data, allowing for the reconstruction of objects and/or anatomical structures in volume. In an embodiment, the higher the resolution, the more detailed the 3D representation may be. Voxel data may be visualized and manipulated to assess internal structures and/or guide medical procedures.

With further reference to FIG. 1, in an embodiment, 3D imaging data may include 2D imaging data that has been transformed into 3D data. For example, this may include 2D ultrasonic images that have been transformed into 3D models. In an embodiment, receiving 2D ultrasonic images and transforming them into 3D models may be consistent with one or more aspects of the process of receiving ultrasonic images described in U.S. patent application Ser. No. 18/938,980, filed on Nov. 6, 2024, titled "APPARATUS AND METHOD OF DETERMINING A CARDIAC IMPLANT SIZE," which is incorporated by reference herein in its entirety.

Still referring to FIG. 1, at least a processor 108 may receive 3D imaging data, which may include a plurality of ultrasonic images. Plurality of ultrasonic images may include, without limitation, a two-dimensional image. As used herein, an "ultrasonic image" is an image generated as a function of a reflection of a sound wave off of a structure. As used herein, an "ultrasonic imaging device" is a device configured to collect ultrasonic images. Non-limiting examples of ultrasonic images and/or imaging techniques include intracardiac echo (ICE) images, transthoracic echocardiograms (TTE), transesophageal echocardiograms (TEE), and point of care ultrasound (POCUS). In some embodiments, plurality of ultrasonic images may include a TEE image. In some embodiments, a TEE image may include a 2D TEE. In some embodiments, a TEE image may include a 3D TEE. In some embodiments, plurality of ultrasonic images may include an ICE image. In some embodiments, a set of ultrasonic images of the patient's organ may include an image selected from the list consisting of a transesophageal echocardiogram image, a transthoracic echocardiogram image, and a point-of-care ultrasound image. An ultrasonic image of plurality of ultrasonic images may depict an organ and/or tissue of a subject. An ultrasonic image of plurality of ultrasonic images may depict a heart, lung, spleen, liver, kidney, muscle, skeleton, intestine, stomach, vein, and/or artery. In some embodiments, an ultrasonic image may depict a heart, and/or a left atrium, left atrial appendage, left ventricle, right ventricle, and/or a right atrium of a heart.

Still referring to FIG. 1, in some embodiments, an ultrasonic image may include transesophageal echocardiogram (TEE) image. In some embodiments, a TEE image may include a view of an ostial diameter and/or length. In some embodiments, plurality of ultrasonic images may include ultrasonic images captured at the same position, and different orientations with respect to a subject's heart. In some embodiments, a TEE image may include a view of an ostial diameter and/or length from one or more angles on a mid-esophageal view. As examples, a TEE image may include a view of a subject's heart and/or an ostial diameter and/or length from 1, 2, 3, 4, 5, 6, 7, 8, 9, or 10 different angles on a mid-esophageal view. In a non-limiting example, a TEE image may include a view of a subject's heart and/or an ostial diameter and/or length from 4 different angles (0°, 45°, 90°,) 135° on a mid-esophageal view. In some embodiments, angles of images may describe a rotational position of an ultrasound transducer relative to a subject's heart. In additional non-limiting examples, a TEE image may include a view of a subject's heart and/or an ostial diameter and/or length from 0° (which may provide a four chamber view), 45-60° (which may provide a two chamber view and in some embodiments may be used to identify a thrombus), 90° (which may provide a long-axis view), 120-135° (which may provide a long-axis view of a left atrial appendage) and/or 135-160° (which may provide an aortic valve long axis view) on a mid-esophageal view. In some embodiments, an ostial diameter and/or length includes an ostial diameter and/or length of a left atrial appendage (LA A) of a heart and/or another location at which a cardiac implant may be placed. In some embodiments, TEE images may include a view of an ostial diameter and/or length from 4 different angles, such as, as a non-limiting example, 0°, 45°, 90°, and 135°. TEE imaging is discussed further with respect to FIG. 5.

Still referring to FIG. 1, in some embodiments, plurality of ultrasonic images may include an intracardiac echocardiography (ICE) image. As used herein, an "ICE image" is an ultrasound image obtained from within the heart's chambers or blood vessels. In some cases, ICE images may be captured using a specialized catheter equipped with an ultrasound transducer that is inserted into the body and guided to the heart of subject. In an embodiment, an ultrasound image may provide a detailed and real-time visualization of cardiac anatomy. ICE images may also include internal structures, functions, and blood flow patterns of the heart of a subject. Plurality of ultrasonic images may be related in terms of content, time of capture, sequence, or any other relevant parameters described herein. In a non-limiting example, each image of plurality of ultrasonic images may represent a particular view, angle, or perspective of an object, subject, or scene, and may be in two-dimensional (2D) or 3D format. Images of plurality of ultrasonic images may include, without limitation, any two-dimensional or three-dimensional images of any anatomy or anatomical structure, including without limitation images of any internal organ, tissue including without limitation muscular, connective tissue, epithelial tissue, and/or nervous tissue, bone, and/or any other element that may be imaged within a human and/or animal body.

Still referring to FIG. 1, in a non-limiting example, structures of a heart of a subject which may be imaged may include chambers (e.g., four chambers including left and right atria and left and right ventricles), valves (i.e., the structures that regulate blood flow between chambers and vessels, including mitral, tricuspid, aortic, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), LAA and other appendages, pathological features (e.g., any abnormalities, defects, and/or the like), and/or other components of a heart.

Still referring to FIG. 1, in an embodiment, each ultrasonic image of plurality of ultrasonic images may include a particular view of subject's heart chambers, valves, vessels, and/or the like. In a non-limiting example, plurality of ultrasonic images may include multiple views e.g., different angles and perspectives of a subject's heart. In another embodiment, plurality of ultrasonic images may be arranged in a temporal sequence. In a non-limiting example, plurality of ultrasonic images may include a series of images captured over time, allowing for an observation of dynamic cardiac functions such as beating, blood flow, and/or the like. In some cases, each ultrasonic image of plurality of ultrasonic images may include a corresponding timestamp, wherein the timestamp may include an indicator showing a date and time of when the corresponding ultrasonic image was taken.

Still referring to FIG. 1, in some embodiments, plurality of ultrasonic images may be received from an electronic health record database. For example, plurality of ultrasonic images may be collected at a first point in time, stored in an electronic health record database, and later used in further steps of a process described herein. In some embodiments, plurality of ultrasonic images may be collected using an ultrasonic imaging device as part of an ultrasonic procedure. An "ultrasonic procedure," as used throughout this disclosure, refers to a medical diagnostic or therapeutic technique that uses high-frequency sound waves to visualize internal structures, assess organ function, or guide treatment within the body. For example, in diagnostic applications, an ultrasound probe may emit sound waves that penetrate the body, and the echoes that bounce ack are recorded and translated into images. These images may help detect abnormalities such as tumors, cysts, and/or blood flow issues. In a therapeutic application, ultrasound may be used for ultrasonic procedures such as ultrasound-guided biopsies, where the ultrasound may help precisely locate the area for sample collection, and/or in lithotripsy, where focused sound waves break up kidney stones. In an embodiment, ultrasonic images may be received from an ultrasonic procedure device 128. For example, ultrasonic procedure device 128 may provide ultrasound imaging data related to echocardiograms and/or the like.

Still referring to FIG. 1, in some embodiments, receiving plurality of ultrasonic images may involve one or more image preprocessing steps. In some cases, at least a processor 108 may be configured to calibrate one or more ultrasonic images of plurality of ultrasonic images by correcting for distortions and/or ensuring accurate spatial representation of a heart of a subject. In a non-limiting example, at least a processor 108 may select one or more reference objects within ultrasonic image which need calibration to correct spatial distortions. In some cases, at least a processor 108 may be configured to place a phantom with predetermined dimensions in an ultrasonic image and adjust ultrasonic image until the phantom's dimensions are accurately represented. In another non-limiting example, an ultrasonic images' brightness and/or contrast may be adjusted by at least a processor 108 to ensure that echogenicity (reflectivity) of the tissues is accurately represented. One or more tissues with known echogenicity may be selected by at least a processor 108 as reference tissues to adjust corresponding portions of the one or more ultrasonic images. In other cases, standardized correction curves may be applied in order to correct the echogenicity of ultrasonic images. As an ordinary person skilled in the art, upon reviewing the entirety of this disclosure, may be aware of various calibration techniques, such as, without limitation, temporal calibration, geometric calibration, among others that can be used by at least a processor 108 to preprocess plurality of ultrasonic images.

Still referring to FIG. 1, receiving plurality of ultrasonic images may include performing image segmentation on or more ultrasonic images of plurality of ultrasonic images. In some cases, image segmentation may include separating specific structures or regions of interest (ROI) from the background or other structures in a given ultrasonic image. In a non-limiting example, at least a processor 108 may be configured to use edge detection algorithms to outline the heart chambers, separating them from surrounding tissues. One or more filters may be applied to highlight the boundaries between different types of tissues during the segmentation. In other non-limiting examples, valves and vessels may also be segmented by applying thresholding techniques. At least a processor 108 may be configured to set an intensity threshold based on the known echogenicity of blood and vessel walls and select pixels or regions having intensity below or above the intensity threshold from the given ultrasonic image. In some cases, one or more machine-learning models may be used to perform image segmentations, for example, and without limitation, a U-net (i.e., a convolution neural network containing a contracting path as an encoder and an expansive path as a decoder, wherein the encoder and the decoder forms a U-shaped structure).

Still referring to FIG. 1, at least a processor 108 may be configured to generate a 3D model representing a heart of a subject as a function of plurality of ultrasonic images. In a non-limiting example, 3D model may include a 3D voxel occupancy representation (VOR). As used in this disclosure, a "3D voxel occupancy representation (VOR)" of anatomy is a 3D digital representation of a spatial structure of the anatomy, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of a heart. In some cases, voxel may be a smallest distinguishable box-shaped part (i.e., 1px·1px·1px) of a three-dimensional image. In some cases, each voxel of plurality of voxels within VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for at least a processor 108 to process.

Still referring to FIG. 1, each voxel of plurality of voxels within VOR may include one or more embedded values. As used herein, "embedded values" refers to specific numerical or categorical data associated with each voxel. In some cases, embedded values may represent various attributes or characteristics of the corresponding portion of structure that voxel represents. In a non-limiting example, embedded values may include density values, intensity values, texture information, or any other quantitative measures that provide insights into the underlying tissue. Such embedded values may be derived from set of ultrasonic images or other imaging modalities used to generate data structure. In some cases, embedded values may be utilized, by at least a processor 108, to differentiate between different types of tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

Still referring to FIG. 1, in an embodiment, each voxel of plurality of voxels may include a presence indicator. As used in this disclosure, a "presence indicator" refers to a data element that indicates a presence or absence (i.e., occupancy) of tissue within that portion. In some cases, and without limitation, presence indicator may include an occupancy status as one of the embedded values described herein. Portion may include a specific location within 3D space where data structure is generated; for instance, and without limitation, a coordinate in 3D space represented in a tuple such as (x, y, z). In an embodiment, 3D VOR may provide a spatial framework that allows for the modeling and visualization of structure in 3D space. In some cases, 3D model may include a plurality of layers or slices (either horizontal [e.g., xy plane] or vertical [e.g., xz or yz plane depends on the view direction]), wherein each layer or slices of the plurality of layers or slices is corresponding to a different cross-sectional view of a structure of subject, and collectively forming a comprehensive 3D depiction of the structure. In a non-limiting example, 3D VOR having plurality of voxels with presence indicators may indicate whether each voxel in 3D space may be occupied by a part of a structure of subject. A binary value such as 0 or 1 may be configured as presence indicator to show either a pixel of 3D space is occupied (e.g., 1) or empty (e.g., 0). In should be noted that other values may be used as presence indicator such as a Boolean value e.g., TRUE or FALSE.

Still referring to FIG. 1, one or more embedded values, such as, without limitations, occupancy, or density, may be derived from plurality of ultrasonic images described herein by at least a processor 108. In a non-limiting example, determining occupancy status of each voxel of plurality of voxels may include converting set of ultrasonic images to a set of binary images and determining occupancy status of each voxel as a function of the structure of interest's binary value. In some cases, occupancy status may include a value representing the likelihood of occupancy of the corresponding tissue. In another non-limiting example, density may be calculated, by at least a processor 108, for each voxel as a function of the echogenicity of one or more pixels on a given ultrasonic image, wherein, the brightness of the given ultrasonic image may be analyzed since different tissues reflect ultrasound waves differently.

Still referring to FIG. 1, generating 3D model of a subject's heart may include generating a 3D array. In some cases, at least a processor 108 may divide 3D space into a grid of plurality of voxels, each with specific x, y, and z coordinates as embedded values. Each element of 3D array may correspond to a voxel. In some cases, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ultrasonic images of plurality of ultrasonic images.

Still referring to FIG. 1, 3D model of structure may include a 3D grid configured to map presence indicators and/or other embedded values described herein of plurality of voxels (e.g., tissue density, blood flow velocity, echogenicity or acoustic properties, and any other biophysical properties). As used in this disclosure, a "3D grid" refers to a 3D model that divides a given volume (e.g., volume of a structure) into a plurality of discrete units called cells (i.e., volume elements). In an embodiment, each cell within 3D grid may be associated with a distinct voxel. Mapping presence indicators or other embedded values may include assigning each presence indicator or embedded value to each point within 3D grid such as corners of each corresponding cell. Such values may be derived from plurality of ultrasonic images as described above.

Still referring to FIG. 1, cells may be continuous, meaning that one or more cells may represent one or more continuous regions of space rather than discreate, separate units. In a non-limiting example, instead of being uniform, mapped presence indicator and/or other embedded values may vary continuously across different cells or cell's volume. In such an embodiment, at least a processor 108 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

Still referring to FIG. 1, 3D model of a heart may include a 3D grid having a plurality of cells e.g., voxels, wherein each cell may contain a continuous range of values representing tissue density, blood flow velocity, or other properties (i.e., embedded values). At least a processor 108 may be configured to apply trilinear or tricubic interpolation to estimate tissue density within each cell based on presence indicator or other known values at the cell's boundaries, since tissue densities change gradually; Such 3D grid may provide a smooth, continuous representation of heat's internal structures, allowing for more nuanced analysis and visualization as described below. In a further embodiment, 3D grid with continuous cells may be additionally used in fluid dynamics simulations.

Still referring to FIG. 1, presence indicators and/or other embedded values may be mapped to a 3D grid as a function of array masking. In a non-limiting example, at least a processor 108 may generate a mask e.g., a binary array that defines which voxels or cells are affected. M ask may be used to select or modify specific voxels or cells based on certain attributes; for instance, and without limitation, at least a processor 108 may use a mask to isolate the LA within the heart focusing the analysis on that specific region. Such mask may include criteria defined by specific density thresholds that distinguish the LA's tissue (i.e., voxels representing LA in 3D grid) from surrounding structures (i.e., neighboring voxels). In some cases, such mask may further include a binary mask, wherein each voxel in the 3D grid may be assigned a first presence indicator such as 1 if the voxel meets the criteria for the LA and a second presence indicator such as 0 if it does not. In some embodiments, mask may be directly applied to 3D grid, selecting, or modifying voxels or cells, thereby enabling at least a processor 108 to highlight, exclude, or otherwise manipulate specific parts of a heart within 3D grid. At least a processor 108 may then perform an element-wise multiplication between 3D grid and the mask. Continuing from the previous non-limiting example, voxels corresponding to the LA (wherein the mask value is 1) may retain their original values, while other voxels (where the mask value is 0) may be set to 0 or other specific value (i.e., excluded or masked out).

Still referring to FIG. 1, in some embodiments, 3D grid may include one or more spatial features extracted from plurality of ultrasonic images. As used in this disclosure, "spatial features" are specific characteristics or attributes related to the spatial arrangement, shape, size, texture, or orientation of structures within a 3D space. In some cases, spatial features may include one or more embedded values described herein and their combinations thereof. In a non-limiting example, spatial features may be represented numerically as a vector, a metric or other mathematical constructs that capture specific spatial characteristics. In some cases, spatial features may also be visualized as contours, surfaces, or other geometric representations. In an embodiment, spatial features may be extracted using edge detection, texture analysis, or other image processing techniques (e.g., cleaning and enhancing images, image segmentation, and/or the like). In another embodiment, one or more machine learning models, such as convolutional neural networks (CNNs) as described in further detail below, may be used to extract complex spatial features.

Still referring to FIG. 1, in a non-limiting example, one or more spatial features may include one or more shape features (i.e., characteristics related to the shape of specific structures), such as curvature, surface area, volume, and/or the like. In another non-limiting example, one or more spatial features may include one or more texture features (i.e., characteristics related to the texture or pattern within tissues, as seen in plurality of ultrasonic images), such as gray-level co-occurrence matrix (GLCM) features representing the texture of heart muscle tissue. In another non-limiting example, one or more spatial features may include one or more orientation features (i.e., characteristics related to the orientation or alignment of structures), such as the angle or alignment of the septum within the heart. In a further non-limiting example, one or more spatial features may include one or more edge and boundary features (i.e., Characteristics related to the edges or boundaries between different structures), such as edge detection features highlighting the boundary between the myocardium and the cardiac chambers. As an ordinary person skilled in the art, upon reviewing the entirety of this disclosure, will be aware of various spatial features extracted from plurality of ultrasonic images consistent with this disclosure.

In further reference to FIG. 1, at least a processor 108 is configured to generate, using plurality of 3D imaging data 124, ultrasound simulation data 132. As used herein, "ultrasound simulation data" refers to pseudo ultrasound data simulated from other imaging data. In an embodiment, ultrasound simulation data 132 may be generated as a function of 3D imaging data, specifically CT imaging data. In an embodiment, ultrasound simulation data 132 may include ultrasound data 136 and probe position data 140. As used throughout this disclosure, "ultrasound data" refers to one or more of real, measured acoustic signals captured during an ultrasound procedure or synthetic or reconstructed data derived from processing 3D imaging data 124. For example, ultrasound data 136 may include the actual imaging obtained from ultrasound signals, such as sound waves emitted by the probe and the echoes that return from tissues and ultrasound data 136 may include imaging data, echo signal data, brightness mode image data, doppler ultrasound data, 3D/4D ultrasound data, elastography (tissue stiffness) data, motion mode data, tissue characterization and imaging parameters, quantitative measurements, time and motion data, color doppler data, power doppler data, color-enhanced ultrasound data, and/or other associated data. Additionally, and/or alternatively, ultrasound data 136 may include pseudo data, such as 3D reconstructed images, surface models, fusion data, and/or the like. In one or more embodiments, ultrasound data 136 may include TEE data, CT data, point-of-care ultrasound data, and/or the like. Further, in some embodiments, this data may mimic what would be obtained from real ultrasound scans but may include pseudo data generated from plurality of 3D imaging data 124. "Probe position data," as used herein, refers to the spatial information about a simulated ultrasound probe's location and/or orientation. For example, probe position data 140 may include, without limitation, spatial coordinates, orientation and angle, probe position in relation to the body, tracking data, probe depth and pressure, probe type and configuration, ultrasound beam direction, tracking system integration data, calibration information, temporal data, and/or other associated data. In an embodiment, probe position data 140 may record the ultrasound probe's movements, angles, and/or the depth of the scanning field, ensuring accurate representation of how different probe positions may affect the ultrasound image. This data may allow for dynamic visualizations and interactions, mimicking how a real ultrasound probe is used during an actual clinical procedure.

In further reference to FIG. 1, in an embodiment, probe position data 140 may include a position and orientation of a simulated ultrasound probe in relation to at least a 3D model of the plurality of 3D models 144 and one or more movements of the ultrasound probe in relation to at least a 3D model of the plurality of 3D models 144. In an embodiment, probe position data 140 may capture both static and/or dynamic information. For example, position may include the spatial coordinates of the ultrasound probe at a given moment in time, indicating its location relative to a target 3D model. This may aid in mapping the exact placement of the probe relative to a patient and/or a specific region of interest within the model. Orientation may include the angular position and/or rotation of the ultrasound probe, in some cases, orientation may be represented as a set of angles and/or rotation matrix that describes the ultrasound probe's angle relative to a reference plane, such as the anatomical position of a patient and/or a model. The orientation may ensure that the ultrasound probe is aligned correctly for imaging from the appropriate angle. One or more movements may include data describing the continuous and/or discrete movements of an ultrasound probe over time in relation to a 3D model. For example, this may include the trajectory and/or path taken by the ultrasound probe, as well as changes in orientation as a user manipulates the ultrasound probe. Further, one or more movements may help track how the ultrasound probe is swept across the model and/or how it rotates. In an embodiment, the ultrasound probe position data 140 may be tied to one or more 3D models representing the anatomy or organs of interest. The 3D models may include models derived from plurality of 3D imaging data 124, which may, in some cases, include 3D models constructed from 2D images/scans. By integrating probe position data 140 with plurality of 3D models 144, it may be possible to visualize the exact positioning and movements of the ultrasound probe during the scanning process.

Still referring to FIG. 1, in an embodiment, probe position data 140 may include one or more movements of the ultrasound probe over time, wherein each position and orientation is correlated to a corresponding temporal element. As used herein, a "temporal element" refers to any component, factor, or aspect that is related to time. For example, temporal elements may refer to time itself, the passage of time, and/or any events and/or changes that occur and/or evolve over time. For example, a temporal element may refer to timestamps, time-based triggers, and/or any data that is indexed and/or processed with respect to time, such as real-time data, time-series data, and/or the time interval between events. In an embodiment, a temporal element may correspond to a time step, and at least a processor 108 may continuously update the position and orientation of the ultrasound probe based on real-time inputs. A "time-step," as used throughout this disclosure, refers to a fixed or variable interval of time used to update data at regular intervals. Each time-step may represent a moment in the system's real-time operation, and it may be used to guide when and how new measurements and/or updates are made. For example, in an ultrasound system, a time-step may correspond to the frame rate of the imaging system, which may dictate how frequently the system updates the position and orientation of the ultrasound probe. In an embodiment, real-time inputs may come from sensors, cameras, and/or tracking systems attached to the ultrasound probe. Additionally, and/or alternatively, these systems may be simulated in the case of a simulation. These inputs may capture the position and orientation of the ultrasound probe at each time-step. These sensors may include accelerometers, gyroscopes, magnetometers, and/or external tracking systems that provide continuous feedback about the ultrasound probe's movements relative to a reference 3D model and/or physical space. In an embodiment, at least a processor 108 may take incoming sensor data at each time-step, compute the new position and orientation of the ultrasound probe, and update the system's 100 state. This may allow system 100 to maintain an up-to-date and accurate representation of the ultrasound probe's location and movement in space. At least a processor 108 may use time-step data to calculate the ultrasound probe's new position based on its previous position and any changes detected by the sensors. Similarly, at least a processor 108 may update the ultrasound probe's orientation based on the real-time input from the sensors. If the ultrasound probe is rotated and/or tilted in any direction, at least a processor 108 may recalculate its orientation at each time-step.

With further reference to FIG. 1, in an embodiment, during an ultrasound scan, system 100 may track static probe position, as well as continuously monitoring dynamic movements, such as the ultrasound probe's shifts in space and/or rotations, along with how these movements correspond to the structures within the 3D model. These aspects may be useful in a variety of scenarios. For example, this may be useful in guiding a clinician, reconstructing detailed images, and/or improving ultrasound navigation systems. By providing real-time feedback on where the ultrasound probe is and how it relates to a 3D model, this data may help clinicians make better decisions about ultrasound placement, which may ensure more accurate scans. Further, system 100 may use the position and orientation data to create more accurate 3D visualizations, such as 3D models, of the scanned area, potentially improving diagnostic accuracy. By integrating movement and position data, system 100 may be used to create an intuitive interface that tracks the ultrasound probe's path through 3D volume, assisting in multi-planar imaging and/or visualizing the anatomy in 3D as the ultrasound probe moves.

In further reference to FIG. 1, in an embodiment, at least a processor 108 may be configured to repeatedly update the position and orientation of the ultrasound probe as a function of sweep trajectory simulation model 152 and the time-step vector. In an embodiment, at least a processor 108 may track the ultrasound probe's current position and orientation in real-time as it moves according to a predefined and/or simulated sweep path, which may be defined by sweep trajectory simulation model 152. At each time-step in the vector, at least a processor may calculate the new position and orientation of the ultrasound probe. For example, if the ultrasound probe is moved and/or rotated, at least a processor may update the position and orientation based on sweep trajectory simulation model 152. These updates may allow continuous adjustments to the scan to ensure the ultrasound probe is imaging the right areas in the correct orientation, which may ensure consistent and/or accurate data collection.

With continued reference to FIG. 1, in an embodiment, generating ultrasound simulation data 132 may include finite element modeling (FEM). "FEM," as used herein, is a method that simulates how sound waves propagate through different tissues in the body. By creating a detailed computational model of the human body, or specific organs, FEM may simulate how ultrasound waves interact with various tissue types, how they are reflected, and/or how echoes return to the probe. The result may include a synthetic representation of how an ultrasound image may appear.

In further reference to FIG. 1, in an embodiment, generating ultrasound simulation data 132 may include ray tracing and acoustic propagation models. "Ray tracing," as used throughout this disclosure, is a method that models the path of sound waves as they travel through tissues and interact with structures, such as organs, muscles, and blood vessels. "Acoustic propagation models," as used herein, is a method used to simulate how sound waves are reflected, refracted, or absorbed by different materials. In an embodiment, acoustic propagation models may generate ultrasound images that mimic real-life scans.

Continuing to reference FIG. 1, generating ultrasound simulation data 132 may include generating ultrasound signals based on predefined tissue characteristics. For example, predefined tissue characteristics may include elasticity, density, and/or speed of sound. These signals may be processed to simulate how an ultrasound system may capture the resulting echoes and translate them into an image. Further, in some embodiments, generating ultrasound simulation data 132 may include generating ultrasound simulation data 132 from reference data. For example, real ultrasound scans and/or other related data from medical imaging databases 120, may be used as reference points. By modifying these images based on simulated probe positions, angles, and/or tissue alterations, synthetic ultrasound images may be generated for specific scenarios, such as different pathologies and/or anatomical variations.

Still referring to FIG. 1, in an embodiment, generating ultrasound simulation data 132 may include using one or more machine-learning algorithms to generate simulated ultrasound images. By training one large dataset, machine-learning algorithms may create synthetic images based on a given input, such as probe position, tissue type, and/or pathology. For example, and without limitation, a generative adversarial network (GAN) 180 may be used to generate ultrasound simulation data 132. In an embodiment, a GAN 180 may include both a generator and a discriminator. The generator may include a neural network designed to produce synthetic ultrasound data 136, such as images. Given certain inputs such as probe position, tissue type, and/or pathology, the generator may learn to create realistic ultrasound images that mimic the appearance of real ultrasound scans. In an embodiment, the generator may use training data, such as real ultrasound images, to capture the characteristics and nuances of how tissues and/or structures appear on ultrasound. In an embodiment, real ultrasound images may be obtained from one or more databases 120, and/or in real-time during an ultrasound procedure. The discriminator may include a neural network tasked with distinguishing between real ultrasound images and the synthetic images generated by the generator. In an embodiment, the discriminator may evaluate the quality of the generated images by comparing them to a dataset of real ultrasound images. The goal of the discriminator is to correctly classify whether an image is real or generated. Once a threshold is met, wherein the discriminatory is unable to discern the difference between real data and synthetic data at a certain ratio, the generator is stabilized and ready to produce synthetic ultrasound simulation data 132 at an acceptable level of "realness."

In further reference to FIG. 1, in an embodiment, training the GAN 180 may include a training process, wherein the training process follows a progression such that the generator creates a simulated ultrasound image, and the discriminator assesses whether the image is realistic or not. The generator and the discriminator may be trained in tandem; the generator improves by trying to "trick" the discriminator, while the discriminator improves by becoming better at distinguishing real from fake images. Over time, this process may aid the generator in producing high-quality synthetic ultrasound images that are virtually indistinguishable from real images. In an embodiment, the generator may receive additional inputs, such as probe position and orientation, tissue type, and/or pathological conditions. Further, a suitable loss function for training the GAN 180 may combine adversarial loss and possibly content loss.

With further reference to FIG. 1, in an embodiment, after generating ultrasound simulation data 132, the ultrasound simulation data 132 may be run through physical models and/or physics-based models to ensure realistic parameters. These models may be designed to simulate real-world phenomena by incorporating the fundamental principles of physics, ensuring that the simulation follows the correct lays of nature. Further, in some embodiments, these models may be integrated with the simulation to ensure realistic parameters.

With continued reference to FIG. 1, in an embodiment, at least a processor 108 is configured to generate, using the ultrasound simulation data 132, a plurality of 3D models 144. As used herein, a "3D model" is a digital representation of an object or environment in three-dimensional space. In an embodiment, a 3D model may include vertices, edges, and faces that define the shape and structure of an object. These elements may be arranged in a 3D coordinate system (x, y, z) to describe the geometry of a model. In an embodiment, generating a plurality of 3D models 144 may include creating a volumetric representation of a scanned anatomical structure, such as a heart. For example, a 2D slice may be stacked and/or stitched together in 3D space, using the probe position data 140 to guide how the slices should be oriented and/or aligned. In an embodiment, if a cardiac ultrasound is being used, multiple 2D images of the heart's chambers and valves may be taken from various angles. These images combined with the probe position data 140 and movement data, may be processed to create a 3D model of the heart.

In continued reference to FIG. 1, in an embodiment, the reconstruction process may implement techniques such as surface rendering and/or volume rendering. "Surface rendering," as used herein, is a technique used in 3D computer graphics and medical imaging to create a visual representation of the surface of a 3D object or model. In an embodiment, surface rendering may include extracting and displaying the outermost layer of a 3D model. In one or more embodiments, surface rendering may utilize a mesh of polygons that define the shape of an object. The surfaces may be shaded and/or textured, highlighting the shape and contours of the structures. As used throughout this disclosure, "volume rendering" is a 3D visualization technique used to represent volumetric data, where the entire volume of an object or structure is visualized, rather than just its surface. Unlike surface rendering, which may only display the outer boundaries, volume rendering may generate images by processing data from the interior of a 3D model. For example, volume rendering may take into account the density and/or other properties of each voxel within the volume. In an embodiment, volume rendering may be applied to data obtained from CT, M RI, and/or ultrasound scans to visualize internal structures, such as organs, blood vessels, and/or tumors, in full 3D.

With further reference to FIG. 1, in an embodiment, plurality of 3D models 144 may be generated from ultrasound data 136 using a 3D model generation model. In an embodiment, 3D generation model may include a machine-learning model. Further, in one or more embodiments, 3D generation model may include a statistical shape model (SSM). In an embodiment, 3D model generation model may be consistent with 3D model generation disclosed in U.S. patent application Ser. No. 18/376,688, filed on Oct. 4, 2023, and entitled "APPARATUS AND METHODS FOR GEN- ERATING A THREE-DIMENSIONAL (3D) MODEL OF CARDIAC ANATOMY VIA MACHINE-LEARNING," the entirety of which is incorporated herein by reference.

Still referring to FIG. 1, 3D model generation model may include a computer vision module. For the purposes of this disclosure, a "computer vision module" is a computational component designed to perform one or more computer vision, image processing, and/or modeling tasks. In one or more embodiments, computer vision module may receive plurality of ultrasound simulation data 132 and generate a plurality of 3D models 144 as a function of a set of images (and associated metadata). In one or more embodiments, computer vision module may include an image processing module, wherein images, such as heart images, may be pre-processed using the image processing module. For the purposes of this disclosure, an "image processing module" is a component designed to process digital images such as heart images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate a plurality of 3D models 144, one or more image processing tasks, such as noise reduction, contrast enhancement, intensity normalization, image segmentation, and/or the like, may be performed by computer vision module on a plurality of CT scans to isolate heart and major vascular structures from surrounding tissues. In one or more embodiments, one or more machine learning models may be used to perform CT scans segmentations, for example, and without limitation, a U-net (i.e., a convolution neural network containing a contracting path as an encoder and an expansive path as a decoder, wherein the encoder and the decoder forms a U-shaped structure).

With continued reference to FIG. 1, in one or more embodiments, a plurality of 3D models 144 may be received from a statistical shape model. For the purposes of this disclosure, a "statistical shape model (SSM)" is a data structure representing, including, and/or utilizing a mathematical model that captures principal modes of variation in shape across a population of similar three-dimensional structures, such as cardiac anatomies. SSM may capture a plurality of 3D models 144. In one or more embodiments, SSM may be used to capture the variability in anatomical structures among different patients; for instance, SSM of a human heart may be constructed from a plurality of heart images collected from a plurality of individuals. In one or more embodiments, when plurality of 3D models 144 represents a heart, the plurality of 3D models 144 generated from SSM may capture an "average" heart shape and main ways in which heart shapes may vary among plurality of individuals. In a nonlimiting example, SSM described herein may be consistent with any SSM disclosed in U.S. patent application Ser. No. 18/376,688, filed on Oct. 4, 2023, and entitled "APPARATUS AND METHODS FOR GENERATING A THREE-DIMENSIONAL (3D) MODEL OF CARDIAC ANATOMY VIA MACHINE-LEARNING", the entirety of which is incorporated herein by reference.

With continued reference to FIG. 1, in one or more embodiments, SSM may be generated by at least a processor 108 as a function of a set of labeled example shapes, each in a form of point-based representations or meshes. In one or more embodiments, example shapes may be represented in a 3D voxel occupancy representation (VOR). In one or more embodiments, plurality of 3D models 144 may include a VOR of patient's heart. For the purposes of this disclosure, a "3D voxel occupancy representation" is a 3D digital representation of a spatial structure of the cardiac anatomy of a heart, wherein the representation is composed of a plurality of discrete volumetric elements known as voxels. For the purposes of this disclosure, a "voxel" is a 3D equivalent of a pixel used in 2D imaging. While a pixel represents a point in a 2D image and may include properties such as color and/or brightness, a voxel may represent a volume in a 3D space and may include additional properties such density/occupancy as described below. In one or more embodiments, each voxel within a plurality of voxels in 3D VOR may represent a specific portion of a heart.

With continued reference to FIG. 1, in one or more embodiments, when plurality of 3D models 144 and/or SSM represents a heart, segmentation of the heart may include a plurality of pixel values, e.g., 0~255, each representing a presence of heart tissue at that location. In a nonlimiting example, computer vision module may be configured to generate a mesh representation of a patient's heart based on plurality of CT scan segmentations or other image segmentations, wherein the mesh representation may include a 3D VOR, as described above, using Pix2V ox. Additionally, or alternatively, exemplary computer vision tasks may include, without limitation, object recognition, feature detection, edge/corner detection, and the like. Nonlimiting examples of feature detection may include scale invariant feature transform (SIFT), canny edge detection, Shi Tomasi corner detection, and/or the like. In one or more embodiments, generating mesh representation of patient's heart may include employing, by computer vision module, one or more transformations to orient one or more images with respect to a 3D coordinate system; exemplary transformations include without limitation homography transforms and affine transforms. Computer vision module may implement one or more 3D modeling algorithms, such as without limitation, marching cubes, contour detection and segmentation, active contour models, and/or the like to generate a coherent 3D representation based on mesh representation of an object, e.g., plurality of 3D models 144. In one or more embodiments, generic 3D modeling techniques may be applied by computer vision module to generate plurality of 3D models 144. In one or more embodiments, generic 3D modeling techniques may include surface modeling, solid modeling, parametric modeling, among others. A person of ordinary skill in the art, upon reviewing the entirety of this disclosure, will be aware of various image processing, computer vision, and modeling tasks that may be performed by at least a processor 108 to generate plurality of 3D models 144 from a set of images such as heart images.

With continued reference to FIG. 1, in one or more embodiments, voxel may be a smallest distinguishable box-shaped part (i.e., 1px x 1px) of a 3D representation of heart. In one or more embodiments, each voxel within a plurality of voxels in 3D VOR may be represented as a cube or rectangular prism (although other shapes may be used in specialized applications). Each voxel may include a size that determines the resolution of a 3D model. In one or more embodiments, smaller voxels may provide higher resolution; however, it may require more computational resources (e.g., RAM) for at least a processor 108 to process. In one or more embodiments, each voxel may include one or more embedded values (i.e., specific numerical or categorical data associated with each voxel). In one or more embodiments, embedded values may represent various attributes or characteristics of the corresponding portion of heart that voxel represents. In a nonlimiting example, embedded values may include density values, intensity values, texture information, or any other quantitative measures that provide insights into the underlying content (e.g., tissue). In another nonlimiting example, each voxel may include a presence indicator, i.e., a data element that indicates a presence or absence (i.e., occupancy) of content within a portion of an object (e.g., heart), as described in U.S. patent application Ser. No. 18/376,688. Such embedded values may be derived from corresponding labels of example shape.

With continued reference to FIG. 1, in one or more embodiments, at least a processor 108 may be configured to align a set of labeled example shapes to a common reference frame using rigid, affine, or otherwise nonrigid registration methods to generate SSM. For example, and without limitation, rigid registration may involve translations and rotations to superimpose the shapes; affine registration may incorporate scaling, shearing, and other linear transformations; nonrigid methods may employ B-splines, thin-plate splines, or diffeomorphic transformations to flexibly map one shape onto another. In one or more embodiments, an averaged position of each corresponding point (or voxel) across all example shapes may be calculated using formula $$\bar{p}_i = \frac{1}{N}\sum_{j=1}^{N} p_{ji}, \text{ where } \bar{p}_i$$

is the mean position of the ith point (or voxel), $p_{ji}$ is the position of the ith point in the jth example shape, and N is the total number of example shapes in the labeled set. In one or more embodiments, principal component analysis (PCA) may be applied to the aligned shapes to extract at least a primary mode of variation. For the purposes of this disclosure, a "primary mode of variation" is a mode of variation that has the most significant variability. For the purposes of this disclosure, a "mode of variation" is a specific pattern or direction of a shape change. In one or more embodiments, such significancy may be indicated by a first principal component in PCA. In one or more embodiments, a plurality of modes of variation may be extracted, wherein each mode (or principal component) may represent a specific way a shape may be deformed from a mean shape, determined by one or more eigenvectors of the covariance matrix of the aligned shapes. In a nonlimiting example, eigenvector with the highest eigenvalue may represent a primary mode of variation which captures the largest amount of shape variability within example shapes, while subsequent modes (eigenvectors) capture decreasing amounts of variability.

With continued reference to FIG. 1, in one or more embodiments, once modes of variation are extracted, at least a processor 108 may be configured to create a shape representation for any given shape within a studied class. In one or more embodiments, plurality of 3D models 144 may be constructed using SSM, wherein plurality of 3D models 144 may integrate mean shape and plurality of modes of variation. In a nonlimiting example, plurality of 3D models 144 having a shape S may be mathematically represented as $$S = \bar{S} + \sum_{k=1}^{M} a_k \times \phi_{k'}$$

wherein $\bar{S}$ denotes mean shape derived from set of example shapes, M is the number of modes of variation considered, $a_k$ are the coefficients or weights for each mode, and $\phi_k$ are the modes of variation (eigenvectors corresponding to the kth principal component). In one or more embodiments, coefficients $a_k$ may dictate a degree to which each mode of variation is present in shape S. In one or more embodiments, coefficients $a_k$ may vary from positive to negative (or negative to positive) based on a deformation of plurality of 3D models 144 in directions described by each mode of variation. In one or more embodiments, plurality of 3D models 144 may include mean shape as described herein. In one or more embodiments, plurality of 3D models 144 may include a predictive shape that may not have been explicitly seen in example shapes or observations. In one or more embodiments, plurality of 3D models 144 may be in 3D VOR as described above.

With continued reference to FIG. 1, in one or more embodiments, at least a processor 108 may be configured to perform shape extraction from segmented CT scans or other similar medical images, as described above. For example, and without limitation, marching cubes algorithm or similar techniques may be employed to convert a voxel-based representation from CT segmentation into mesh, wherein the mesh may represent the outer surface of patient's heart. In one or more embodiments, mesh may vary in resolution, with more grid capturing finer details. In one or more embodiments, a consistent number of landmark points may be used to represent patient's heart surface. In a nonlimiting example, one or more landmark points may be manually annotated by medical professionals to ensure that the landmark points correspond to specific anatomical locations of patient's heart. In one or more embodiments, one or more landmark points may be automatically derived using one or more computer vision algorithms as described herein. Landmark points may be uniformly spaced across the surface of extracted shape. In one or more embodiments, the size of heart shape may be normalized so that the number of landmark points remain consistent between different heart shapes. In one or more embodiments, SSM may include an implementation of generalized Procrustes analysis (GPA) to find a desired rigid transformation (translation, rotation) that aligns with example shapes. In a nonlimiting example, at least a processor 108 may be configured to minimize the sum of squared distance between corresponding landmark points across each heart shape. In one or more embodiments, size normalization may be reverted after such an alignment. Constructing plurality of 3D models 144 may include combining mean shape computed by averaging positions of corresponding landmarks points and one or more modes of variations. In a nonlimiting example, plurality of 3D models 144 may include a template model generated based on a plurality of standard templates, as described in U.S. patent application Ser. No. 18/376,688.

Further referencing FIG. 1, in an embodiment, at least a processor 108 may generate plurality of 3D models 144 based on different ultrasound images. In some cases, at least a processor 108 may generate plurality of 3D models 144 based on different sets of simulation data. For example, a 3D model of the heart may be generated from different 2D ultrasound images captured from multiple perspectives. In an embodiment, plurality of 3D models 144 may reflect different stages of the procedure and/or different anatomical perspectives, such as preoperative models, intraoperative models, and/or postoperative models.

In continued reference to FIG. 1, in an embodiment, at least a processor 108 is configured to train, using a reinforcement learning algorithm 148, a sweep trajectory simulation model 152. As used herein, a "sweep trajectory" refers to the path or movement pattern followed by an imaging probe or device during a scanning procedure. For example, a scanning procedure may include ultrasound, where the probe moves across and/or around the area of interest to gather data. The sweep trajectory ensures that the device covers a broad area, enabling the collection of detailed data that can be used to create 2D and/or 3D visualizations of internal structures. In medical imaging different sweep trajectories may be chosen based on the anatomical area being studied, such as the heart, liver, and/or fetus, and the type of information needed, such as tissue density, blood flow, and/or organ motion. A "reinforcement learning algorithm" is a type of machine-learning algorithm where an agent learns to make decisions by interacting with an environment. The agent may take actions, receive feedback in the form of rewards and/or penalties, and adjust its behavior over time to maximize cumulative rewards. Key components of reinforcement learning may include the agent, environment, state, action, reward, policy, and/or value function. In reinforcement learning, an "agent," is the decision-maker that preforms actions in the environment. The "environment," as used herein, refers to the system with which the agent interacts. A "state," as used herein, is a representation of the environment at a given time. "Action," as used herein, refers to the choices the agent can make to affect the environment. As used herein, "reward" refers to the feedback the agent receives after taking an action, indicating how good or how bad that action was. A "policy," as used herein, is a strategy or mapping from states to actions that the agent follows to decide what actions to take. As used herein, a "value function" is a measure of the long-term reward an agent can expect from a given state, guiding the agent's decision making. In an embodiment, a reinforcement learning algorithm 148 aims to find an optimal policy that maximizes the total expected reward over time, in some cases using techniques such as Q-learning, deep Q networks (DQN), and/or policy gradient methods.

As a non-limiting example, reinforcement learning (RL) algorithm 148 may be applied to train the sweep trajectory simulation model 152 to optimize the path a catheter should follow during medical procedures. For example, the RL agent may be the sweep trajectory simulation model 152. The environment may include 3D anatomical data provided by the 3D imaging data and 3D models. The state may be represented by the position of a catheter at any given point in the procedure, as well as surrounding tissue structures derived from the probe position data 140 and 3D models. The actions may include potential movements and/or changes in a catheter's trajectory. The RL model may decide on the best action, such as direction, angle, and/or path, which the catheter should take based on a current state. The reward may include a signal given to the agent based on the success of its action. For example, a positive reward may be given for actions that move the catheter closer to the target area while avoiding obstacles and/or scans that provide a thorough view. Alternatively, negative rewards may be assigned when the catheter comes too close to obstacles and/or deviates from the optimal path, which could reduce the success of the procedure. The policy may include the strategy that the RL agent learns to determine the best sequence of actions to reach the target area while avoiding obstacles. In an embodiment, the optimal trajectory may be the policy that maximizes the cumulative reward, meaning it leads to the most successful catheter sweeps in the fewest steps. During training, the sweep trajectory simulation model 152 may interact with the environment. Over time, through trial and error, the sweep trajectory simulation model 152 may learn which actions lead to successful catheter sweeps. Further, the sweep trajectory simulation model 152 may use the training data, which may include 3D imaging, probe position data 140, and 3D models to learn patterns and optimize its trajectory. The training may involve optimizing the sweep trajectory simulation model 152 to find the best trajectory for each procedural scenario, potentially factoring in the number of sweeps needed to achieve an accurate 3D model and/or successful procedure.

In continued reference to FIG. 1, in an embodiment, RL algorithm 148 may include Q-learning, policy gradient methods, and/or actor-critic methods, each of which may be used to train an RL agent, such as sweep trajectory simulation model 152. "Q-learning," as used herein, is an off-policy, model-free reinforcement learning algorithm that focuses on learning an action-value function (Q-function). This function may estimate the expected cumulative reward an agent can achieve starting from a specific state, taking an action, and then following the optimal policy from there. The Q-function may represent the expected future rewards for taking a particular action in a given state and following the best possible policy thereafter. The agent may iteratively update its Q-values based on rewards observed from the environment. The update rule used in Q-learning may be derived from the Bellman equation, which allows the agent to adjust its Q-values. In an embodiment, the agent may employ an &-greedy policy, meaning it mostly chooses the action with the highest Q-value but occasionally explores random actions to encourage exploration and avoid getting stuck in suboptimal solutions.

Further referencing FIG. 1, as used herein, "policy gradient methods" are on-policy, model-free reinforcement learning algorithms that focus on directly learning the policy function, which maps states to probabilities of taking each action. Instead of estimating the value function like in other approaches, policy gradient methods may parameterize the policy, in some cases using a neural network, and optimize it by estimating the gradient of the expected return with respect to the policy parameters. The central idea is to adjust the policy in the direction that increases the expected reward. The gradient of the expected reward may be calculated using the likelihood ratio method and/or a REINFORCE algorithm, which updates the policy based on the rewards the agent receives for actions taken in various states.

In continued reference to FIG. 1, as used herein "actor-critic methods" are on-policy, model-free reinforcement learning algorithms that combine the advantages of both value-based methods, such as Q-learning, and policy-based methods, like policy gradient methods. These methods may use two components: the actor and the critic, each serving distinct roles to improve the learning process. The actor may represent the policy, which is responsible for deciding which action to take given a state. The critic, on the other hand, may evaluate the action taken by the actor by estimating the value function and/or the advantage function, which measures how much better or worse a particular action is compared to the average action in that state. The feedback from the critic may help guide the actor's learning. In an embodiment, the critic may calculate the temporal difference (TD) error, which is the difference between the expected reward, based on the current state's value, and the actual reward received. Based on this evaluation, the actor may update its policy using the advantage function to improve future actions.

In further reference to FIG. 1, in an embodiment, training the sweep trajectory simulation model 152 may include training the sweep trajectory simulation model 152 using 3D imaging data, probe position data 140, and plurality of 3D models 144. In some cases, the combination of these datasets may allow sweep trajectory simulation model 152 to learn an optimal trajectory. In an embodiment, optimal trajectory may include the path a catheter should follow to reach its target area while avoiding potential obstacles, such as blood vessel walls, and/or other tissues that may impact the success of a procedure. As used herein, a "catheter" is a thin, flexible tube used in medical procedures to access the heart and blood vessels. In an embodiment, a catheter may include a cardiac catheter. A catheter, as described herein, and its associated data may be consistent with one or more aspects of the catheters as described in U.S. patent application Ser. No. 18/920,065, filed on Oct. 18, 2024, titled "SYSTEMS AND METHODS FOR ARTIFICIAL INTELLIGENCE ASSISTED MEDICAL DEVICE LOCALIZATION," which is incorporated by reference herein in its entirety. In an embodiment, the training data may allow the sweep trajectory simulation model 152 to learn optimal sweep trajectories that yield an accurate 3D model. Further, in some cases, the trajectories may be optimized as a function of a number of sweeps.

With continued reference to FIG. 1, sweep trajectory simulation model 152 may be configured to output a time-step vector 156 relating to the movement of a catheter. As used herein, a "time-step vector" refers to a representation of discrete points in time within a sequence or simulation. Here, time-step vector 156 may include a mathematical object that may store multiple values, such as the state of a system, at different time steps in a simulation and/or model. For example, time-step vector 156 may include a mathematical representation of a catheter's movement at each time point. In an embodiment, time-step vector 156 may include information such as the position of a catheter in 3D space, the orientation of a catheter, the velocity or speed of movement, and/or the direction of movement. The velocity or speed of movement, in some cases, may be used to calculate the distance the catheter will travel in between time steps. Further, the direction of movement may indicate the trajectory the catheter is following at each specific time step. In an embodiment, the time-step vector 156 may serve as a guiding parameter for controlling a catheter's real-time movement during a procedure. Further, system 100 may use these vectors to simulate how a catheter should be maneuvered over time, making adjustments as necessary based on feedback from the environment.

In further reference to FIG. 1, in an embodiment, at least a processor 108 may be configured to generate ultrasound simulation data 132 which may include, in some cases, expert data 160. Further, in an embodiment, training sweep trajectory simulation model 152 May include training sweep trajectory simulation model 152 using an imitation learning algorithm using the expert data 160.As used herein, "expert data" refers to information, insights, or knowledge that is provided by individuals with specialized expertise in a particular field or subject. This data may be captured from professionals, practitioners, and/or researchers who have in-depth experience, training, and/or education in a given domain, and can offer high-quality, reliable, and accurate information based on their expertise. For example, here, expert data 160 may be captured from an echocardiographer. An "echocardiographer," as used throughout this disclosure, is a trained medical professional who specialized in performing echocardiograms, which are ultrasound examinations of the hearth. In some cases, cardiologists may also perform and/or oversee echocardiograms. In an embodiment, expert data 160 may be captured from recorded ultrasound scans, annotations and/or labels, and/or motion trajectories. For example, videos and/or sensor data capturing the actual movements and/or gestures of the ultrasound probe as performed by experts, and associated metadata, may be captured during one or more procedures and/or from a database 120. Further, experts may annotate specific movements and/or critical positions of the ultrasound probe during a scan, marking key anatomical regions and/or particular maneuvers. In some cases, expert data 160 may include data from motion tracking devices, such as optical tracking systems, accelerometers, and/or gyroscopes, attached to the ultrasound probe that track the ultrasound probe's movements in 3D space during a scan.

With continued reference to FIG. 1, in an embodiment, training sweep trajectory simulation model 152 may include feeding the captured expert data 160 into sweep trajectory simulation model 152 so that it learns the various nuances of ultrasound probe movement. For example, this may include smooth trajectories, optimal angles and/or orientations, and/or realistic dynamics. In an embodiment, sweep trajectory simulation model 152 may include a machine-learning model. For example, in some cases, sweep trajectory simulation model 152 may include a neural network 172, wherein the neural network 172 includes an input layer configured to receive a set of features related to a position, orientation, and motion trajectory of an ultrasound probe, one or more hidden layers configured to process and transform the set of features, and an output layer configured to generate a prediction for at least a subsequent movement of the ultrasound probe as a function of the set of features. Further, in some embodiments, the neural network 172 may include a training module configured to adjust one or more weights of the neural network 172 by comparing the prediction for at least a subsequent movement of the ultrasound probe to an actual probe movement during simulation.

In further reference to FIG. 1, in an embodiment, the reinforcement learning algorithm 148 may train a reinforcement learning model 176, wherein the reinforcement learning model 176 includes a state representation that defines a current position, orientation, and trajectory of the ultrasound probe within a simulation as a function of the plurality of 3D imaging data 124 and real-time inputs from ultrasound simulation data 132, an action space that represents a set of possible movements that can be made to the position and orientation of the ultrasound probe during the simulation, a reward function that evaluates a quality metric of one or more movements of the ultrasound probe based on predefined goals, and a policy that governs how the reinforcement learning model 176 selects actions based on a current state, wherein the policy is learned over time by interacting with the simulation and receiving feedback from the reward function. Further, in some cases, the reinforcement learning model 176 may include a training process, wherein the training process includes iteratively adjusting the policy as a function of one or more movements of the ultrasound probe, wherein the one or more movements are associated with positive and negative feedback.

With further reference to FIG. 1, in an embodiment, RL model 176 may include a model-based framework. M odel-based algorithms may enable the agent to predict the outcomes of actions and select those that maximize rewards.

These algorithms may be considered greedy, as decisions are made solely to maximize the reward. M odel-based algorithms may be the most effective in environments where the agent has complete knowledge about the system and the consequences of its actions, making them ideal for static and/or fixed environments. M odel-based methods may also allow for proactive planning, as they rely on understanding the environment to make decisions ahead of time. Alternatively, in some embodiments, RL model 176 may include a model-free framework 168. M odel-free framework 168 may involve the agent taking multiple actions over time and learning from the resulting outcomes. Rather than relying on a model of the environment, these algorithms may focus on trial and error, developing a strategy or policy to maximize reward points based on the agent's experiences. Model-free framework 168 may be better suited for dynamic environments where the agent doesn't have full knowledge, such as in autonomous driving, where traffic patterns can change unpredictably. These algorithms may excel in situations where the environment is complex and constantly evolving.

In further reference to FIG. 1, in an embodiment, at least a processor 108 may be configured to train sweep trajectory simulation model 152 using a model-free framework 168, wherein the model-free framework 168 includes generating a policy based on trial-and-error interactions with a simulated environment, updating the policy iteratively by observing rewards and state transitions from the simulated environment and adjusting the policy to maximize cumulative rewards, employing an exploration-exploitation strategy to balance exploration of new trajectories and exploitation of known, high-reward trajectories, and using a value function to estimate the expected reward for state-action pairs, and adjusting the policy accordingly. As used herein, "trial-and-error interactions" refer to a learning process in which an agent repeatedly attempts different actions or behaviors in an attempt to achieve a desired outcome. In an embodiment, each action may be evaluated based on the result it produces, and the agent may adjust its behavior accordingly. Over time, through repetition, the agent may refine its approach by identifying which actions lead to successful outcomes and which do not. "State transitions," as used throughout this disclosure, refer to the process of moving from one state to another in a system. A "state," as used herein is a specific configuration or condition of the system at a given point in time, representing all relevant variables or features that define the system's situation. In an embodiment, a state transition may occur when the system changes from one state to another as a result of an action taken by an agent, process, and/or external input. In an embodiment, an exploration-exploitation strategy may include a fundamental concept of reinforcement learning and/or decision-making problems, where an agent must balance two competing approaches, exploration and exploitation. "Exploration," as used herein, refers to the agent trying out new actions or strategies that it has not tried before in order to gather more information about the environment. Exploration may aid the agent in discovering potentially better actions and/or states that it has not et encountered, thereby improving its overall understanding of the environment. As used throughout this disclosure, "exploitation" refers to the agent choosing actions that it already knows will give it the highest reward based on its past experiences. Exploitation may leverage the agent's current knowledge of the environment to maximize short-term gains. However, it may prevent the agent from discovering potentially better options that may lead to higher, long-term rewards.

In continued reference to FIG. 1, in an embodiment, reinforcement learning may include imitation learning. Imitation learning may be useful in situations wherein rewards are sparse, for example in autonomous driving. Instead of learning from sparse rewards and/or manually specifying a reward function, an expert may provide a set of demonstrations. The agent may then attempt to learn the optimal policy by following and/or imitating the expert's decisions. In an embodiment, the environment in which the agent operates may be modeled as a Markov Decision Process (MDP). An MDP may include states(S), actions (A), transition model (P(s'|s,a)), and reward function (R(s,a)). In such an embodiment, an expert's demonstration may include expert data 160, wherein the expert provides a sequence of state-action pairs (trajectories, t) which are used to train the agent. The expert's behavior may be considered to follow an optimal policy ($\pi^*$).

With further reference to FIG. 1, in an embodiment, imitation learning may include behavioral cloning (BC). "BC," as used herein, is the simplest form of imitation learning, where the agent learns from the expert's demonstrated state-action pairs through supervised learning. In an embodiment, the agent may learn to map states to actions by treating the expert's demonstrations as independent and identically distributed. In an embodiment, and exemplary algorithm for BC may include (1) collect demonstrations ($\tau^*$ trajectories) from expert, (2) treat the demonstrations as independent and identically distributed state-action pairs: $(s^*_0, a^*_0), (s^*_1, a^*_1), \ldots$ (3) learn $\pi_\theta$ policy using supervised learning by minimizing the loss function $L(a^*, \pi_0(s))$.

Further, in some embodiments, imitation learning may include direct policy learning (DPL). In an embodiment, DPL is a form of imitation learning, where the agent may interact with an expert during training, such as querying the expert for feedback. This method may use an iterative process to refine the agent's policy. For example, without limitation, the process may follow the following structure: start with an initial policy based on expert demonstrations, roll out the policy in the environment, collect new trajectories, query the expert for feedback to train a new policy, and repeat the process util convergence. An exemplary DPL algorithm may include (1) initial predictor $\pi_0$, (2) for m=1: collect trajectories t by rolling out $\pi_{m-1}$, estimate state distribution $P_m$ using s E $\tau$, collect interactive feedback $\{\pi^*(s)|s\ E\ \tau\}$, data aggregation/train $\pi m$ on $P_l$ U . . . U $P_m$, policy aggregation/train I'm on $P_m$ and $\pi\omega=\beta\pi m'\ m+(1-\beta)\ \pi_{m-1}$. In an embodiment, a DPL process may utilize data aggregation to train the policy on all previously collected data. Alternatively, and/or additionally, a DPL process may blend the current policy with all previous policies, combining them through geometric blending.

In an embodiment, imitation learning may include inverse reinforcement learning (IRL) 164. IRL 164 may include an approach wherein the agent tries to learn the reward function of the environment based on the expert's behavior. The goal may be to derive the reward function that explains the expert's actions and then use reinforcement learning to find the optimal policy that maximizes this reward function. An exemplary process may include beginning with expert demonstrations, learning the reward function that explains the expert's behavior, solving the reinforcement learning problem, comparing the learned policy with the expert's policy, and repeating the process until a good policy is learned. In an embodiment, an IRL 164 algorithm may include the following: (1) collect expert demonstrations: $D=\{\tau_1, \tau_2, \ldots \tau_m\}$ (2) in a loop: learn reward function $r_\theta\{S_t, a_t)$, given the reward function re, learn x policy using reinforcement learning, compare π with π* (expert's policy), STOP if x is satisfactory. In an embodiment, an IRL 164 approach may utilize a model-given approach, wherein it assumes a known reward function and state transition model. Such an embodiment may be suitable for small state spaces. Alternatively, an IRL 164 approach may utilize a model-free approach, wherein it assumes a complex or unknown reward function. Such an embodiment may be modeled with neural networks. Further, a model-free approach may handle large and/or continuous state spaces but may not assume known state transitions.

Further referencing FIG. 1, in an embodiment, at least a processor may be configured to train the sweep trajectory simulation model 152 using IRL 164, wherein training sweep trajectory simulation model 152 using IRL 164 includes receiving expert data 160 representing a set of state-action pairs corresponding to optimal sweep trajectories, estimating a reward function based on the expert data, where the reward function defines the desirability of each state-action pair, iteratively refining the reward function by comparing the outcomes of simulated actions with the expert data 160, using the reward function as a guide, updating the sweep trajectory simulation model 152 by maximizing an expected reward for a trajectory, and evaluating the trained sweep trajectory simulation model 152 by comparing simulated sweep trajectory outputs with expert data 160.

With continued reference to FIG. 1, in an embodiment, once sweep trajectory simulation model 152 is trained, it may receive data from a "real" catheter, ultrasonic probe, and/or the like, and generate a time-step vector. The trained sweep trajectory simulation model 152 may guide clinicians in an ultrasonic procedure by providing optimized sweep trajectories and/or suggested adjustments to a current sweep trajectory.

Figure 2:
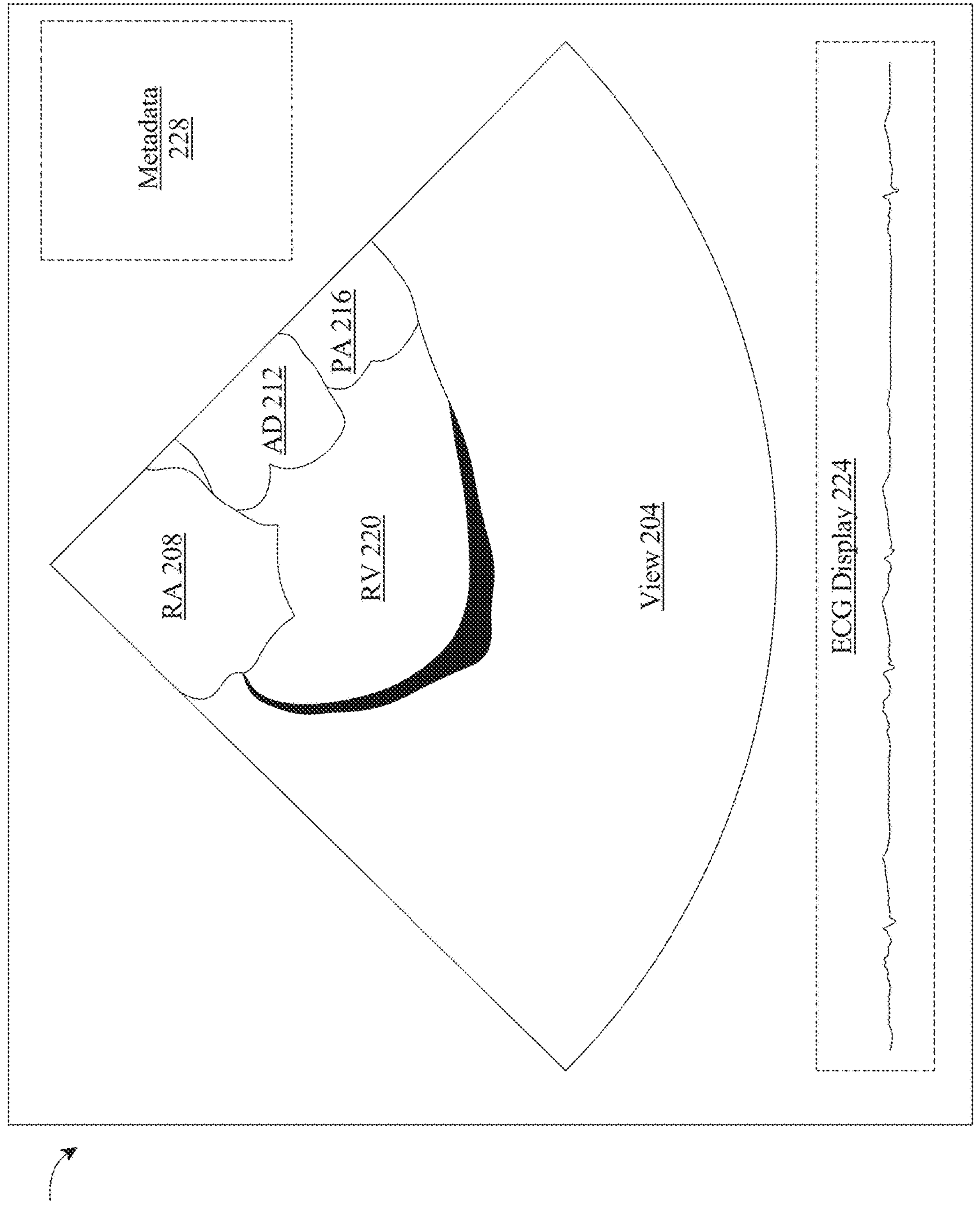
FIG. 2 shows an exemplary embodiment of an intracardiac echocardiography (ICE) image.

Now referring to FIG. 2, an exemplary embodiment of an ultrasonic image such as ICE image 200 is illustrated. As described above with reference to FIG. 1, plurality of ultrasonic images may include a plurality of ICE images, wherein each ICE image of the plurality of ICE images is a specialized form of echocardiography that may provide detailed image of heart's interior structures. In a non-limiting example, plurality of ICE images may include an ICE video (e.g., plurality of ICE images arranged in a corresponding time sequence). In an embodiment, ICE image 200 may be real-time, dynamic ultrasound image that provide a (detailed) view 204 of heart's interior structures, including, without limitation, right atrium (RA) 208, anterior descending (AD) 212, pulmonary atresia (PA) 216, and right ventricular (RV) 220.

With continued reference to FIG. 2, in some cases, ICE image 200 may include gray scaled image. It should be noted that, in some cases, ICE image 200 may be configured to visualize blood flow and/or blood flow patterns within the heart via color doppler. In some cases, resolution and/or clarity of ICE image 200 as described herein may be superior to transthoracic or transesophageal echocardiography due to the ICE catheter may be positioned inside the heart, closer to the structures being imaged.

Still referring to FIG. 2, in a non-limiting example, heart chambers may appear as dark, anechoic (black) areas since they are filled with blood, which doesn't reflect ultrasound waves well. Heart walls, valves, and/or other structures may appear as varying shades of gray, depending on their density and composition, in some cases, Color Doppler overlays may show blood flow in different colors, indicating the direction and speed of blood flow. For instance, and without limitation, red may indicate flow towards the probe, while blue may indicate flow away from the probe.

With continued reference to FIG. 2, in a non-limiting embodiment, ICE image 200 may be synchronized with ECG data, allowing for precise timing of cardiac events with anatomical visualization provided by ICE. In some cases, ICE image 200 may include an ECG display 224 configured to display ECG waveform as a continuous line graph at the top, bottom, or side of ICE image 200. In some cases, specific parts of the cardiac cycle e.g., systole or diastole, may be correlated with visual data from ICE image 200.

Additionally, or alternatively, and still referring to FIG. 2, ICE image 200 may come with accompanying metadata 228 displayed on the side or corners of ICE image 200 as described herein. In some cases, metadata 228 may provide essential contextual information about ICE image 200 and/or the corresponding patient. In a non-limiting example, metadata 228 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace (e.g., ECG data as described above), measurement annotations (e.g., any measurements taken directly on the image e.g., diameter, a value of thickness of a heart wall and the like), image sequence information (e.g., image number, total number of frames, and the like), comments or notes, hospital or clinic information, and/or the like. As an ordinary person skilled in the art, upon reviewing the entirety of this disclosure, will be aware of ICE image 200 and various components thereof may be incorporated by system 100 for generating 3D model of cardiac anatomy.

Figure 3:
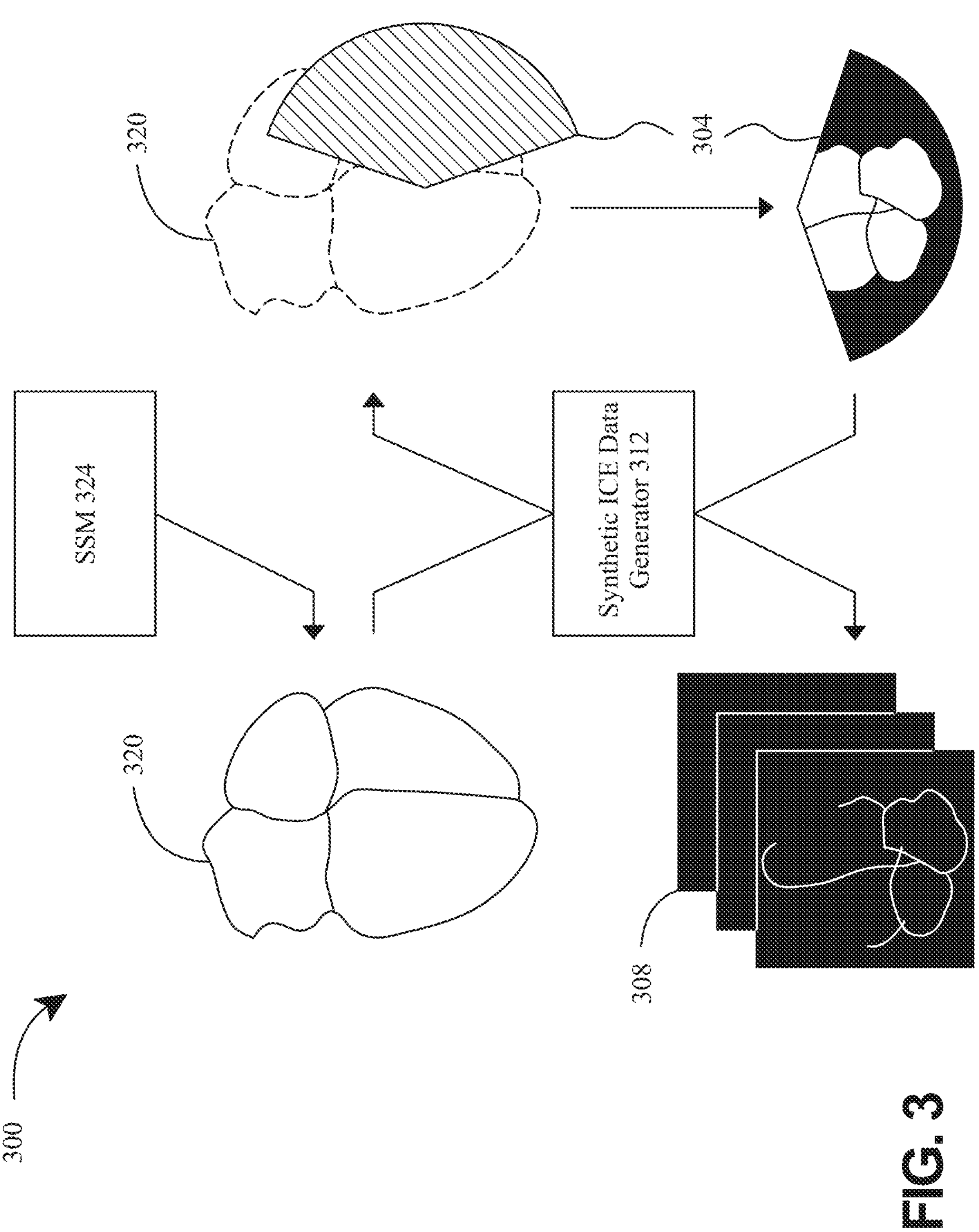
FIG. 3 is a flow diagram of an exemplary embodiment of an ICE image example generation process.

Now referring to FIG. 3, a flow diagram of an exemplary embodiment of an exemplary process 300 for generation of ultrasound data, such as, without limitation, ICE images TEE images, TTE images, POCUS images. In reference to FIG. 3, an ICE imaging modality may be used in an exemplary manner and is not meant to be limiting. The present disclosure supports a variety of imaging modalities including ICE, TEE, TTE, POCUS, and/or the like, and their associated data. In an embodiment, plurality of 3D models may be generated, at least in part, via process 300. In some cases, at least a processor 108 may be configured to receive 3D imaging data, which may include a 3D model of the heart 320, such as any 3D model of heart 320 as described herein and identify an ultrasound view, which may include an ICE view 304 (i.e., visual representation of image obtained using intracardiac echocardiography as described above e.g., ICE image 200) based on the received 3D model. In some cases, 3D model received by at least a processor 108 may be derived from CT scans as described above with reference to FIG. 1. In other cases, processor may receive CT scans directly instead of 3D models. Ultrasound simulation data may be generated by at least a processor 108, which may include a synthetic ICE frame 308, as a function of identified ICE view 304, wherein the synthetic ICE frame 308 may be used as one or more training examples.

With continued reference to FIG. 3, in some cases, at least a processor 108 may interface with one or more 3D models (i.e., detailed representation of heart's anatomy in a 3D space, capturing intricate structures, chambers, vessels, valves, among others) as described above, or other imaging modalities and/or databases, and equipped with algorithms e.g., CNN, gradient boosting machines, SVM, PCA, and/or the like to analyze model's geometry and spatial relationships upon receiving the 3D models. In some cases, 3D models may be received from SSM 324 as described above with reference to FIG. 1 via a communicative connection between at least a processor 108 and SSM 324. In a non-limiting example, at least a processor 108 may be configured to determine an optimal viewpoint or angles from which ICE view 304 would provide a desired diagnostic value or procedural guidance.

Still referring to FIG. 3, in some cases, identification and selection of ICE view 304 may be automatically identified, using one or more machine learning models as described herein. In a non-limiting example, at least a processor 108 may utilize one or more machine learning models trained on cardiac anatomy viewpoints identification training data, wherein the cardiac anatomy viewpoints identification training data may include a plurality of cardiac anatomies as input correlated to a plurality of ICE images as output and identify at least one ICE view 304 (most informative) for a given cardiac anatomy using the trained machine learning models.

Still referring to FIG. 3, in other cases, ICE view 304 may be defined by a user such as a medical professional. In a non-limiting example user interface of display device may allow a user (e.g., a clinician) to manually rotate, pan, and zoom displayed 3D model and/or corresponding CT scans. As user does so, at least a processor 108 may dynamically calculate and displays potential ICE views 304 based on user's chosen perspective. Additionally, or alternatively, depending on cardiac procedure being planned or executed, at least a processor 108 may prioritize certain ICE views 304. For instance, and without limitation, ICE view 304 may be pre-defined. For atrial fibrillation ablation, ICE view 304 may showcase the pulmonary veins' entrances into the LA may be emphasized. In other cases, ICE view 304 may be automatically identified, by at least a processor 108, using one or more machine learning models as described herein, such as, without limitation, synthetic ICE data generator as described in detail below.

With continued reference to FIG. 3, as used in this disclosure, a "synthetic ICE frame" refers to a digitally generated or simulated image that emulates a visual representation obtained from ICE view 304. In some cases, synthetic ICE frames 308 may be produced using computational methods and/or models such as, without limitation, a synthetic ICE data generator 312 based on pre-existing data, models, or simulations e.g., identified ICE views 304. In a non-limiting example, synthetic ICE frames 308 may include a simplified version e.g., an image illustrating heart anatomy via a plurality of lines indicating contours of heart's structure as shown in FIG. 3. One or more image processing techniques and/or computer vision algorithms such as, without limitation, histogram equalization, adaptive filtering, edge detection (e.g., Canny or Sobel operators), contour extraction, and/or the like may be applied, by at least a processor 108, on a segmented CT scan and/or 3D models based on identified ICE view 304. Synthetic ICE frame 308 may be rendered on a blank canvas or background that mimics the echogenicity of an ICE image according to extracted contours, wherein the extracted contours may be represented as a bold lines and enhanced with shading to give depth. In some cases, synthetic ICE frame 308 may be validated and verified by overlaying synthetic ICE frame 308 onto original ICE view 304, ensuring accuracy and resemblance.

Still referring to FIG. 3, in some cases, generating synthetic ICE frames 308 may include implementations of one or more aspects of "generative artificial intelligence," a type of A 1 that uses machine learning algorithms to create, establish, or otherwise generate data. Such data may include, without limitation, ultrasonic image that is similar to one or more provided training examples. In an embodiment, machine learning module described herein may generate one or more generative machine learning models that are trained on one or more set of CT scans and/or 3D models in ICE image view 304 as described above. Synthetic ICE data generator 312 may include one or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 3, in some cases, generative machine learning models within synthetic ICE data generator may include one or more generative models. As described herein, "generative models" refers to statistical models of the joint probability distribution P(X, Y) on a given observable variable x, representing features or data that can be directly measured or observed (e.g. CT scans and/or 3D models derived from CT scans) and target variable y, representing the outcomes or labels that one or more generative models aims to predict or generate (e.g., synthetic ICE frames 308). In some cases, generative models may rely on Bayes theorem to find joint probability; for instance, and without limitation, Naïve Bayes classifiers may be employed by computing device to categorize input data such as, without limitation, CT scans and/or 3D models derived from CT scans into different views.

In a non-limiting example, and still referring to FIG. 3, one or more generative machine learning models may include one or more Naïve Bayes classifiers generated, by at least a processor 108, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P (A)=P(B), where P(A/B) is the probability of hypothesis A given data B also known as posterior probability; P(B/A) is the probability of data B given that the hypothesis A was true; P (A) is the probability of hypothesis A being true regardless of data also known as prior probability of A; and P(B) is the probability of the data regardless of the hypothesis. A naïve Bayes algorithm may be generated by first transforming training data into a frequency table. At least a processor 108 may then calculate a likelihood table by calculating probabilities of different data entries and classification labels. At least a processor 108 may utilize a naïve Bayes equation to calculate a posterior probability for each class. A class containing the highest posterior probability is the outcome of prediction.

Still referring to FIG. 3, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as $P(X, Y)=P(Y)\ [\Pi ip(Xi|Y)$, wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities P(X¿|Y) and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of ICE images based on CT scans and/or 3D models derived from CT scans (e.g., identified ICE views 304), wherein the models may be trained using training data containing a plurality of features of input data as described herein and/or the like correlated to a plurality of ICE views.

Still referring to FIG. 3, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 6-8.

With continued reference to FIG. 3, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 6 to distinguish between different categories e.g., real vs. fake, or states e.g., TRUE vs. FALSE within the context of generated data such as, without limitations, synthetic ICE frames 308, and/or the like. In some cases, at least a processor 108 may implement one or more classification algorithms such as, without limitation, Support Vector Machines (SV M), Logistic Regression, Decision Trees, and/or the like to define decision boundaries.

In a non-limiting example, and still referring to FIG. 3, generator of GAN may be responsible for creating synthetic data that resembles real ICE images. In some cases, GAN may be configured to receive CT scans and/or 3D models derived from CT scans as input and generates corresponding examples of ICE images containing information describing anatomy in different ICE views. On the other hand, discriminator of GAN may evaluate the authenticity of the generated content by comparing it to true ICE images, for example, discriminator may distinguish between genuine and generated content and providing feedback to generator to improve the model performance. Additionally, or alternatively, GAN may include a conditional GAN as an extension of the basic GAN as described herein that allows for generation of ICE images using pre-existing CT scans and/or 3D models derived from CT scans based on certain conditions or labels. In standard GAN, generator may produce samples from random noise, while in a conditional GAN, generator may produce samples based on random noise and a given condition or label.

With continued reference to FIG. 3, in other embodiments, one or more generative models may also include a variational autoencoder (VA E). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VA E may include a second neural network, for example, and without limitation, a decoder, wherein the "decoder" is configured to map from the latent space to the input space.

In a non-limiting example, and still referring to FIG. 3, VAE may be used by at least a processor 108 to model complex relationships between CT scans and/or 3D models derived from CT scans. In some cases, VA E may encode input data into a latent space, capturing example ICE images. Such encoding process may include learning one or more probabilistic mappings from observed CT scans and/or 3D models derived from CT scans to a lower-dimensional latent representation. Latent representation may then be decoded back into the original data space, therefore reconstructing the 3D models representing example ICE images. In some cases, such decoding process may allow VA E to generate new examples or variations that are consistent with the learned distributions.

Additionally, or alternatively, and still referring to FIG. 3, at least a processor 108 may be configured to continuously monitor synthetic ICE data generator. In an embodiment, at least a processor 108 may configure discriminator to provide ongoing feedback and further corrections as needed to subsequent input data. An iterative feedback loop may be created as at least a processor 108 continuously receive real-time data, identify errors (e.g., distance between synthetic ICE frame 308 and real ICE images) as a function of real-time data, delivering corrections based on the identified errors, and monitoring subsequent model outputs and/or user feedbacks on the delivered corrections. In an embodiment, at least a processor 108 may be configured to retrain one or more generative machine learning models within synthetic ICE data generator based on user modified ICE frames or update training data of one or more generative machine learning models within synthetic ICE data generator by integrating validated synthetic ICE frames (i.e., subsequent model output) into the original training data. In such embodiment, iterative feedback loop may allow synthetic ICE data generator to adapt to the user's needs and performance requirements, enabling one or more generative machine learning models described herein to learn and update based on user responses and generated feedbacks.

With continued reference to FIG. 3, other exemplary embodiments of generative machine learning models may include, without limitation, long short-term memory networks (LSTM s), (generative pre-trained) transformer (GPT) models, mixture density networks (M DN), and/or the like. As an ordinary person skilled in the art, upon reviewing the entirety of this disclosure, will be aware of various generative machine learning models that may be used generating synthetic ICE frames 308.

Still referring to FIG. 3, in a further non-limiting embodiment, synthetic ICE data generator 312 may be further configured to generate a multi-model neural network that combines various neural network architectures described herein. In a non-limiting example, multi-model neural network may combine LSTM for time-series analysis with GPT models for natural language processing. Such fusion may be applied by computing device to generate synthetic ICE frames 308. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTM s for sequential pattern recognition, and a M DN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models that may be used to generating synthetic ICE frames 308 as described herein. As an ordinary person skilled in the art, upon reviewing the entirety of this disclosure, will be aware of various multi-model neural network and combination thereof that may be implemented by system 100 in consistent with this disclosure.

Figure 4:
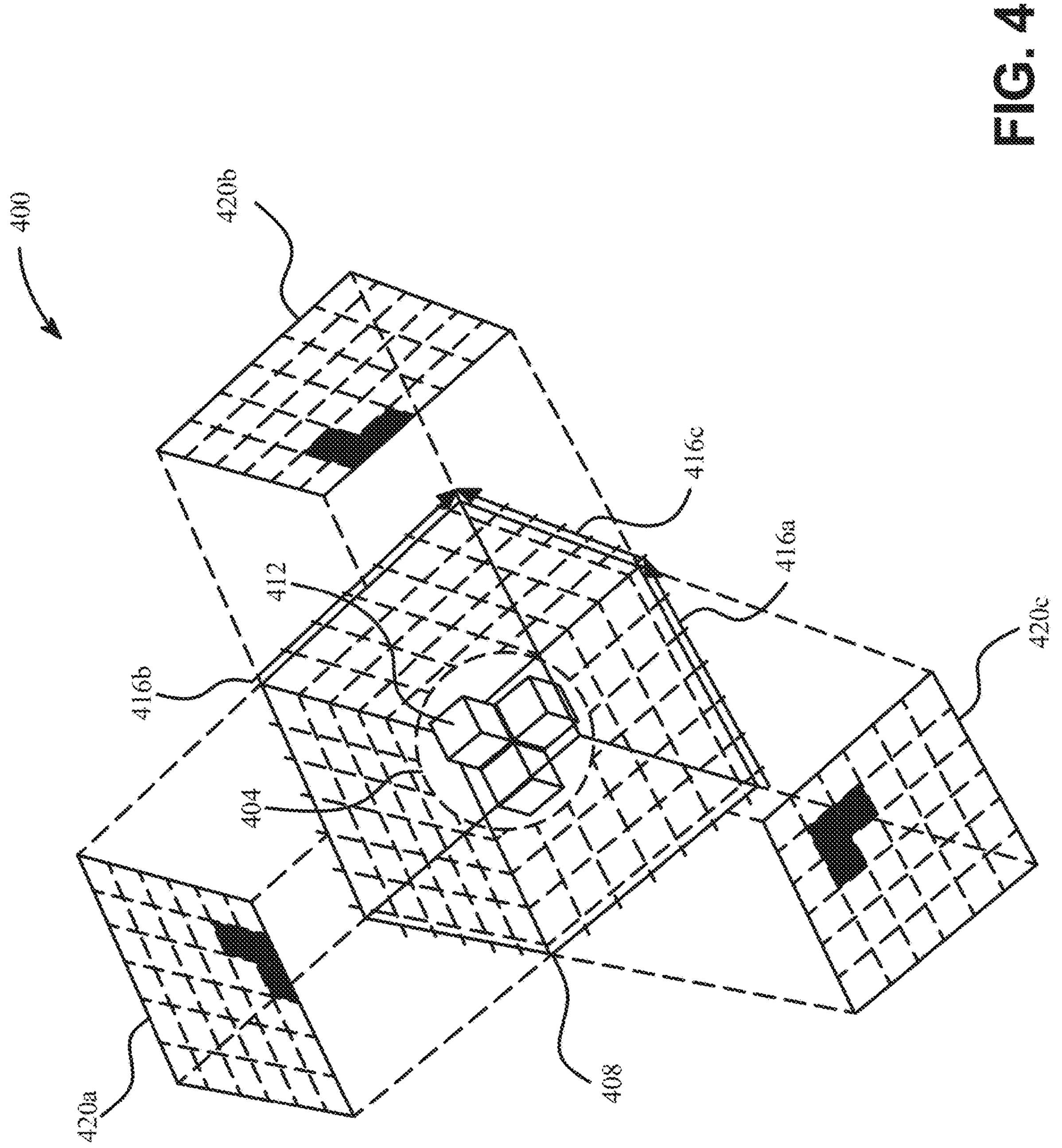
FIG. 4 illustrates an exemplary embodiment of a three-dimensional (3D) voxel occupancy representation.

Now referring to FIG. 4, an exemplary embodiment of a 3D VOR 400 is illustrated. 3D VOR 400 may be used to represent 3D object 404. In an embodiment, 3D VOR 400 may divide a 3D space 408 into a grid of one or more cubic units e.g., voxels 412, wherein each voxel 412 represents a specific volume within 3D space 408. In a non-limiting example, 3D object 404 may include a structure pertaining to a subject.

Still referring to FIG. 4, in some cases, each voxel 412 may act as a basic building block. In a non-limiting example, each voxel 412 may be configured to represent a discrete portion of 3D space 408. In an embodiment, each voxel 412 may include a presence indicator, which denotes whether the voxel is occupied or unoccupied. In such embodiment, the binary or continuous value may allow 3D VOR 400 to map the presence or absence of material within each voxel 412, creating a granular representation of 3D object 404.

With continued reference to FIG. 4, in some cases, the resolution of 3D VOR 400 may be determined by the size and number of voxels within the grid. In a non-limiting example, smaller voxel may provide a higher resolution, capturing finer details, while larger voxels offer a more generalized representation.

Figure 5:
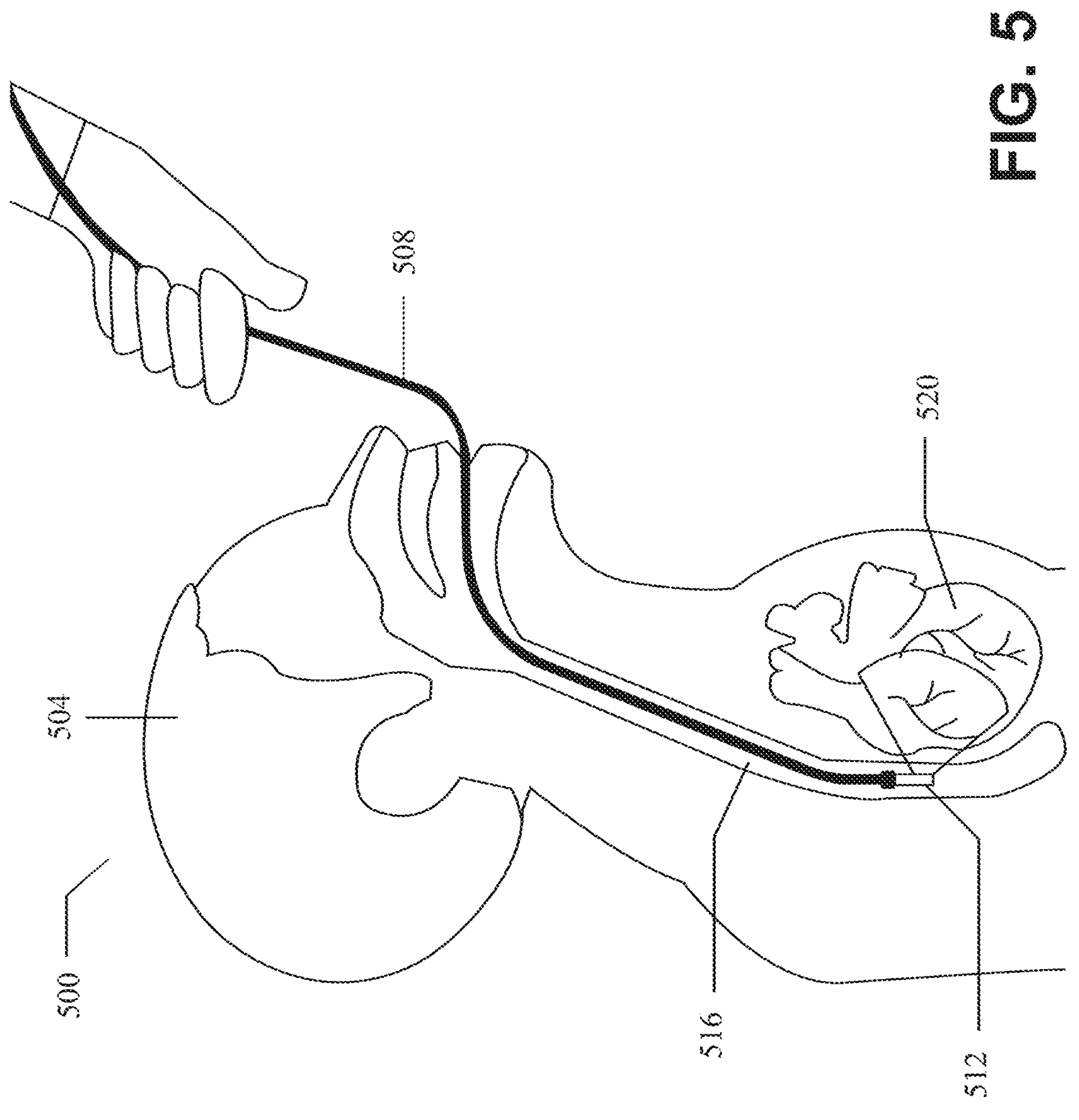
FIG. 5 is a schematic diagram of an exemplary transesophageal echocardiogram.

Now referring to FIG. 5, a schematic of an exemplary transesophageal echocardiogram (TEE) procedure 500 is shown. In some cases, TEE 500 may be performed during another procedure for instance heart surgery. According to some embodiments, a patient 504 has an endoscope 508, with an ultrasonic transducer 512, inserted into his esophagus 516. As one's esophagus 516 is proximal one's heart 520, ultrasonic transducer 512 may generate echocardiograms.

Still referring to FIG. 5, in some embodiments, transesophageal echocardiography (TEE) may provide superior imaging quality than intracardiac echocardiography (ICE), as larger ultrasound transducers 512 may be placed within the esophagus 516 than within heart 520. In some cases, ultrasound transducers must be substantially miniaturized to fit within heart 520, as in ICE catheters. As esophagus 516 may be proximal to heart 520, TEE may provide a clear image of various heart structures without needing vascular access (as commonly required by ICE). Additionally, TEE may be performed without obstructing patient's 504 ribcage and intermediary tissues (as commonly required by transthoracic echocardiography [TTE]). In some cases, TEE images may also provide information associated with angle of acquisition. Angle of acquisition may be an angle of TEE probe with respect to esophagus 516 (e.g., esophageal axis).

Figure 6:
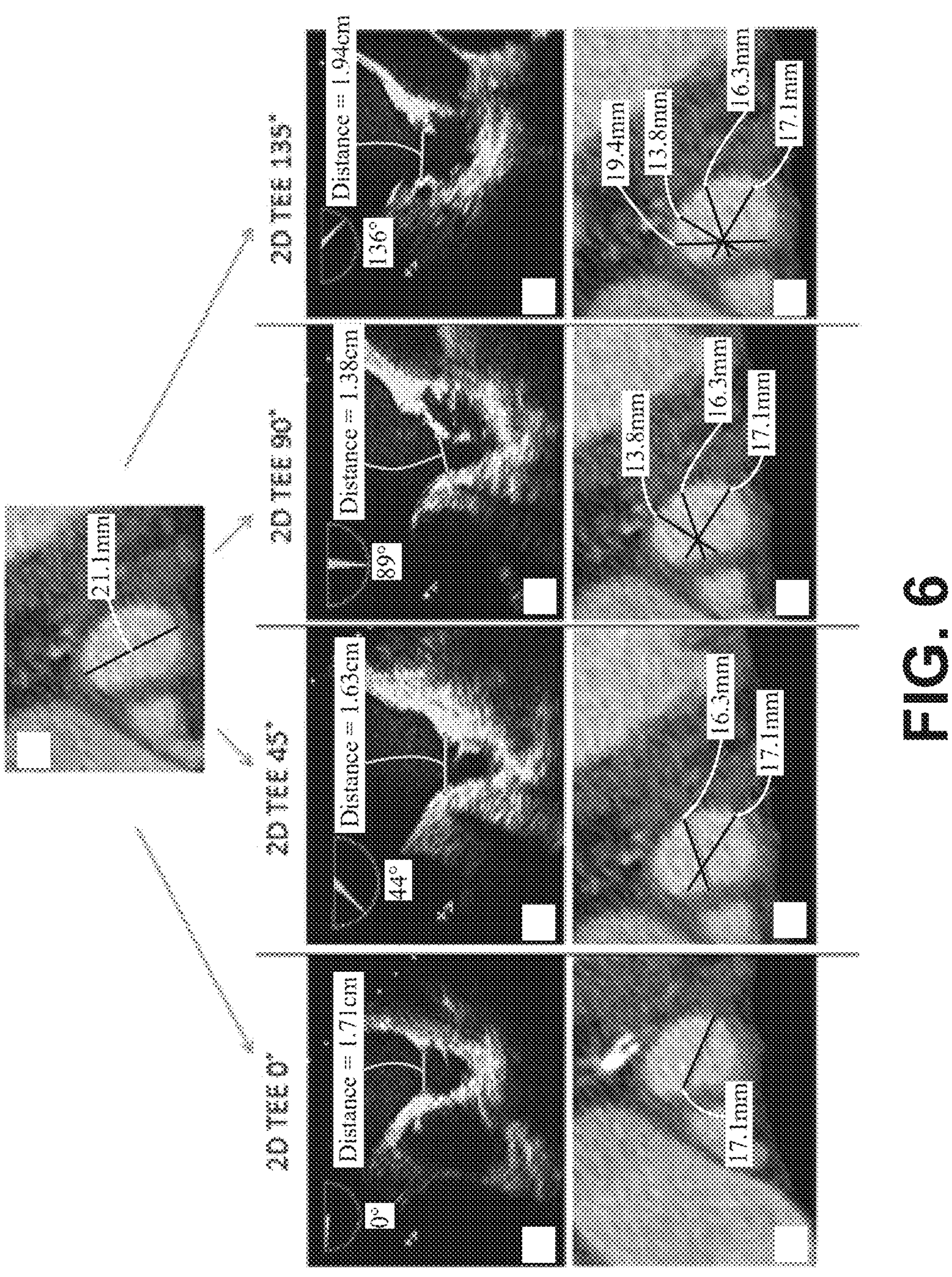
FIG. 6 presents 2D transesophageal echocardiogram (TEE) views at varying orientations.
Figure 7:
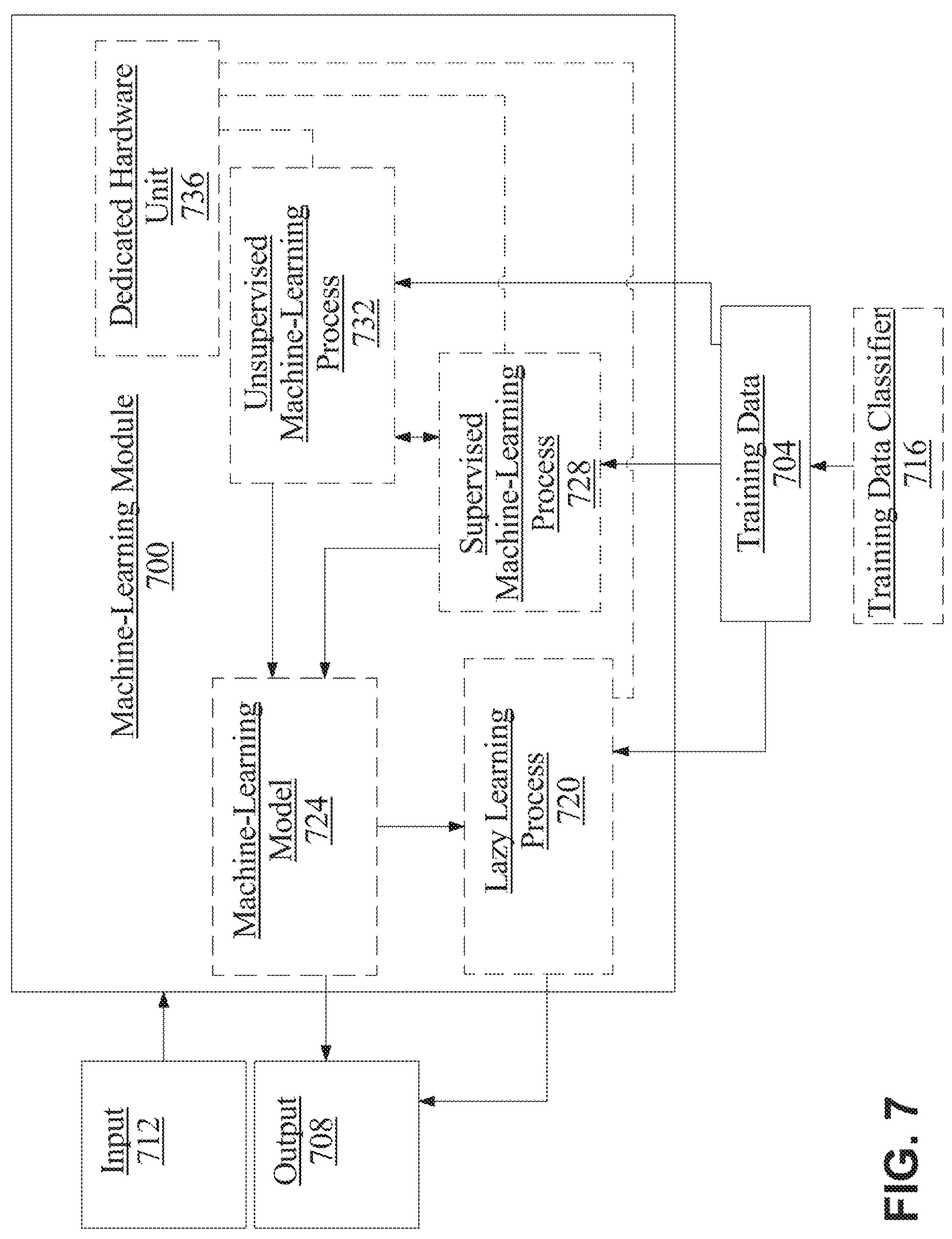
FIG. 7 is a block diagram of an exemplary embodiment of a machine learning model.
Figure 8:
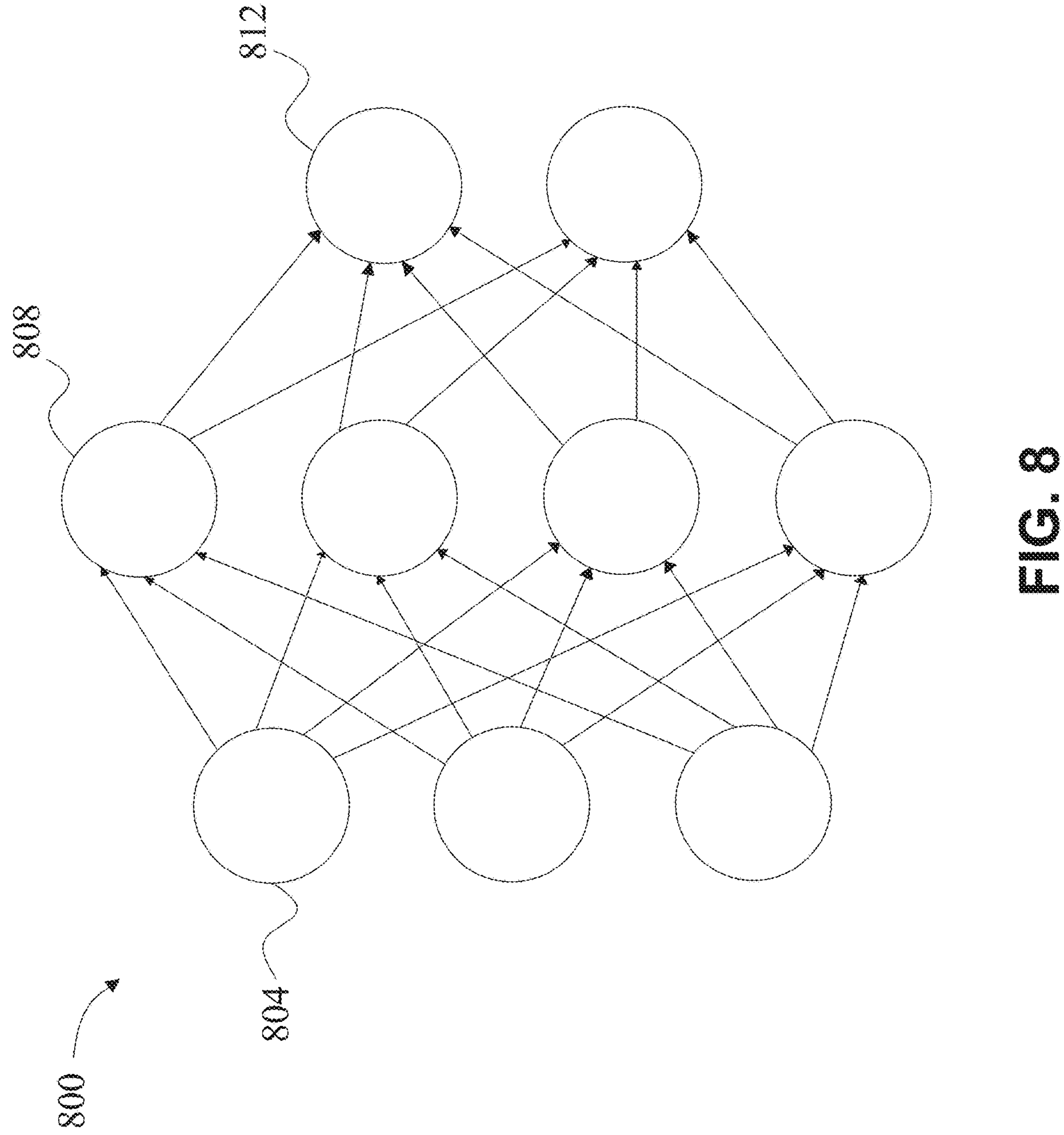
FIG. 8 is a schematic diagram of an exemplary embodiment of a neural network.

Still referring to FIG. 5, in some embodiments, TEE echocardiogram data, including images showing heart structures and, in some cases, angle of acquisition, may be used as input to any machine learning process described in this application, for instance with reference to FIGS. 6-8. For instance TEE echocardiogram data may be used to reconstruct 3D heart models. In some cases, TEE echocardiogram data is input into a machine learning model that outputs a 3D heart model (e.g., 3D mesh model and/or statistical shape model).

Still referring to FIG. 5, in some embodiments, TEE may be a preferred imaging modality for structural heart interventions, such as without limitation left atrial appendage occlusion (LAOO) and aortic/mitral/other heart valve replacement procedures. In some cases, technology and improvements described in this disclosure permit creation and/or modification of a 3D heart mesh from TEE data to aid in planning implant size selection, as well as to guide implantation procedures. In some cases, virtual placement of a 3D model of a candidate implant (such as without limitation LAAO device and/or heart valve implants) can be simulated on a 3D heart model generated by any method described in this disclosure. This novel and improved functionality may validate appropriate size and placement of implants within heart 520, as well as other organs within body of patient 504. For example, in the context of electrophysiology procedures, TEE 500 can be used to create heart anatomical models that can be used as reference for electroanatomic mapping, and guidance of ablation catheters for atrial fibrillation procedures (such as without limitation pulmonary vein isolation).

Still referring to FIG. 5, in some embodiments, applications described with reference to TEE 500 above can be extended for use with TTE and point of care ultrasound (POCUS). In some cases, both TTE and POCUS may acquire ultrasound images of chest/surface of patient 504. In some cases, TTE and POCUS data may be used as an input (and/or training data) for any machine learning process described in this disclosure, for instance with reference to FIGS. 6-8. In some cases, use of TTE and/or POCUS data (in machine learning processes described in this disclosure) may require adjustment in ultrasound acquisition parameters and positions to acquire a sufficient number of frames for 3D reconstruction. In some cases, TTE and POCUS offer improved accessibility (with POCUS being portable/mobile as well) and non-invasive 3D heart modeling, often without anesthesia or sedation, compared to catheterized 3D heart modeling commonly performed today for electroanatomical mapping and ablation procedures.

Still referring to FIG. 4, in an embodiment, voxels 412 may be arranged in a regular pattern along three axis 416*a-c*, each pointing a distinct direction. In a non-limiting example, voxels 412 may be arranged along x, y, and z axes, wherein such arrangement may facilitate efficient manipulation and rendering of the 3D object 404. In some cases, spatial features 420*a-c* such as, without limitation, edges, surfaces, textures, and any other spatial features as described above with reference to FIG. 1, may be extracted from 3D VOR 400 by analyzing the relationships and patterns between neighboring voxels.

Referring now to FIG. 6, multiple 2D transesophageal echocardiogram (TEE) views at varying orientations are presented. Image A demonstrates a maximal LAA diameter of 21.1 mm obtained utilizing the double-oblique multiplanar reconstruction methodology by 3D CT. Panels B-E demonstrate the traditional 2D TEE LAA scanning views of 0°, 45°, 90°, and 135° views reflected on a multiplanar reconstruction of the LAA ostium on 3D CT. In panels F-I, the CT dimensions are taken at a focal intersection point and angled, from 0° (assigned as the measurement of 17.1 mm), and increased by 45° around this focal point for each subsequent measurement. Panel I demonstrate in this patient the 135° TEE measurement of 19.4 mm as off-axis to the true centroid of the LAA, and is not reflective of the maximal LAA width as shown in panel A, thereby resulting in an undersized WATCHMAN device. By CT, this patient would receive a 24 mm device with no peri-watchman leak.

Referring now to FIG. 7, an exemplary embodiment of a machine-learning module 700 that may perform one or more machine-learning processes as described in this disclosure is illustrated. Machine-learning module 700 may perform determinations, classification, and/or analysis steps, methods, processes, or the like as described in this disclosure using machine learning processes. A "machine learning process," as used in this disclosure, is a process that automatedly uses training data 704 to generate an algorithm instantiated in hardware or software logic, data structures, and/or functions that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative example inputs may include 3D imaging data and outputs may include time-step vector relating to the movement of a catheter and/or synthetic 3D models.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to real versus fake 3D models and/or images.

Still referring to FIG. 7, a computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P (A)+P(B), where P(A/B) is the probability of hypothesis A given data B also known as posterior probability; P(B/A) is the probability of data B given that the hypothesis A was true; P (A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 7, a computing device may be configured to generate a classifier using a K-nearest neighbors (K NN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 7, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 7, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 7, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 7, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 7, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 7, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 7, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 7, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 7, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25th percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 7, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

With continued reference to FIG. 7, in one or more embodiments, computing device may implement one or more aspects of "generative artificial intelligence (AI)," a type of AI that uses machine learning algorithms to create, establish, or otherwise generate data such as, without limitation, 3D models and/or the like in any data structure as described herein (e.g., text, image, video, audio, among others) that is similar to one or more provided training examples. In an embodiment, machine learning module described herein may generate one or more generative machine learning models that are trained on one or more set of 3D imaging data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 7, in some cases, generative machine learning models may include one or more generative models. As described herein, "generative models" refers to statistical models of the joint probability distribution P(X, Y) on a given observable variable x, representing features or data that can be directly measured or observed and target variable y, representing the outcomes or labels that one or more generative models aims to predict or generate.

Still referring to FIG. 7, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model.

With continued reference to FIG. 7, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers to distinguish between different categories e.g., real versus fake, or states e.g., TRUE vs. FALSE within the context of generated data such as, without limitations, 3D models, and/or the like. In some cases, computing device may implement one or more classification algorithms such as, without limitation, Support Vector Machines (SV M), Logistic Regression, Decision Trees, and/or the like to define decision boundaries.

In a non-limiting example, and still referring to FIG. 7, generator of GAN may be responsible for creating synthetic data that resembles real 3D models and/or 3D imaging data. In some cases, GAN may be configured to receive 3D imaging data such as, without limitation, 3D and/or 3D scans or images, 3D models, metadata associated with ultrasonic scans, as input and generates corresponding 3D models containing information describing or evaluating the performance of one or more 3D models. On the other hand, discriminator of GAN may evaluate the authenticity of the generated content by comparing it to real 3D models, for example, discriminator may distinguish between genuine and generated content and providing feedback to generator to improve the model performance.

With continued reference to FIG. 7, in other embodiments, one or more generative models may also include a variational autoencoder (VA E). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VA E may include a second neural network, for example, and without limitation, a decoder, wherein the "decoder" is configured to map from the latent space to the input space.

In a non-limiting example, and still referring to FIG. 7, VAE may be used by computing device to model complex relationships between 3D imaging data. In some cases, VAE may encode input data into a latent space, capturing 3D models. Such an encoding process may include learning one or more probabilistic mappings from observed 3D imaging data to a lower-dimensional latent representation. Latent representation may then be decoded back into the original data space, therefore reconstructing the 3D imaging data. In some cases, such decoding process may allow VAE to generate new examples or variations that are consistent with the learned distributions.

With continued reference to FIG. 7, in some embodiments, one or more generative machine learning models may be trained on a plurality of 3D imaging data as described herein, wherein the plurality of 3D imaging data may provide visual information that generative machine learning models analyze to understand the dynamics of 3D imaging data, including how 2D images/scans may fit together as a 3D model. Additionally, or alternatively, one or more generative machine learning models may utilize one or more predefined templates representing, for example, and without limitation, correct 3D models. In a non-limiting example, one or more expert sweep trajectories (i.e., predefined models or representations of correct and ideal sweep trajectories corresponding to 3D model) may serve as benchmarks for comparing and evaluating plurality of 3D imaging data.

Still referring to FIG. 7, computing device may configure generative machine learning models to analyze input data such as, without limitation, 3D imaging data to one or more predefined templates such as expert sweep trajectories representing correct 3D models described above, thereby allowing computing device to identify discrepancies or deviations from accurate 3D models. In some cases, computing device may be configured to pinpoint specific errors in 3D imaging data or any other aspects of the 3D imaging data. In a non-limiting example, computing device may be configured to implement generative machine learning models to incorporate additional models to detect probe position and/or orientation and output indicators such as, without limitation, visual indicator, audio indicator, and/or any other indicators as described above. Such indicators may be used to signal the detected error described herein.

Still referring to FIG. 7, in some cases, one or more generative machine learning models may also be applied by computing device to edit, modify, or otherwise manipulate existing data or data structures. In an embodiment, output of training data used to train one or more generative machine learning models such as GAN as described herein may include expert sweep trajectories associated with 3D models that linguistically or visually demonstrate 3D imaging data. In some cases, 3D models may be synchronized with 3D imaging data, for example, and without limitation, in a side-by-side or even overlayed arrangement with the input user action data, providing real-time visual guidance.

Additionally, or alternatively, and still referring to FIG. 7, computing device may be configured to continuously monitor 3D imaging data. In an embodiment, computing device may configure discriminator to provide ongoing feedback and further corrections as needed to subsequent input data. In some cases, one or more sensors such as, without limitation, wearable device, motion sensor, or other sensors or devices described herein may provide localization data that may be used as subsequent input data or training data for one or more generative machine learning models described herein. An iterative feedback loop may be created as computing device continuously receive real-time data, identify errors as a function of real-time data, delivering corrections based on the identified errors, and monitoring user response and/or device response signal on the delivered corrections. In an embodiment, computing device may be configured to retrain one or more generative machine learning models based on receipt of additional 3D imaging data or update training data of one or more generative machine learning models by integrating expert sweep trajectories and/or simulated movements into the original training data. In such embodiment, iterative feedback loop may allow machine learning module to adapt to the user's needs and performance, enabling one or more generative machine learning models described herein to learn and update based on 3D models and generated feedback.

With continued reference to FIG. 7, other exemplary embodiments of generative machine learning models may include, without limitation, long short-term memory networks (LSTM s), (generative pre-trained) transformer (GPT) models, mixture density networks (M DN), and/or the like. As an ordinary person skilled in the art, upon reviewing the entirety of this disclosure, will be aware of various generative machine learning models may be used to generate synthetic 3D imaging data and/or 3D models.

Still referring to FIG. 7, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate 3D models. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a M DN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models may be used to generate synthetic data as described herein. As an ordinary person skilled in the art, upon reviewing the entirety of this disclosure, will be aware of various multi-model neural network and combination thereof that may be implemented by system 100 in consistent with this disclosure.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

With further reference to FIG. 7, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a “convergence test” is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 7, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 732 may not require a response variable; unsupervised processes 732 may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, A daBoost, gradient tree boosting, and/or voting classifier methods. Machine-learning algorithms may include neural net algorithms, including convolutional neural net processes.

Still referring to FIG. 7, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. A ny technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 7, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 7, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 7, one or more processes or algorithms described above may be performed by at least a dedicated hardware unit 736. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 736 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 736 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 736 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 9:
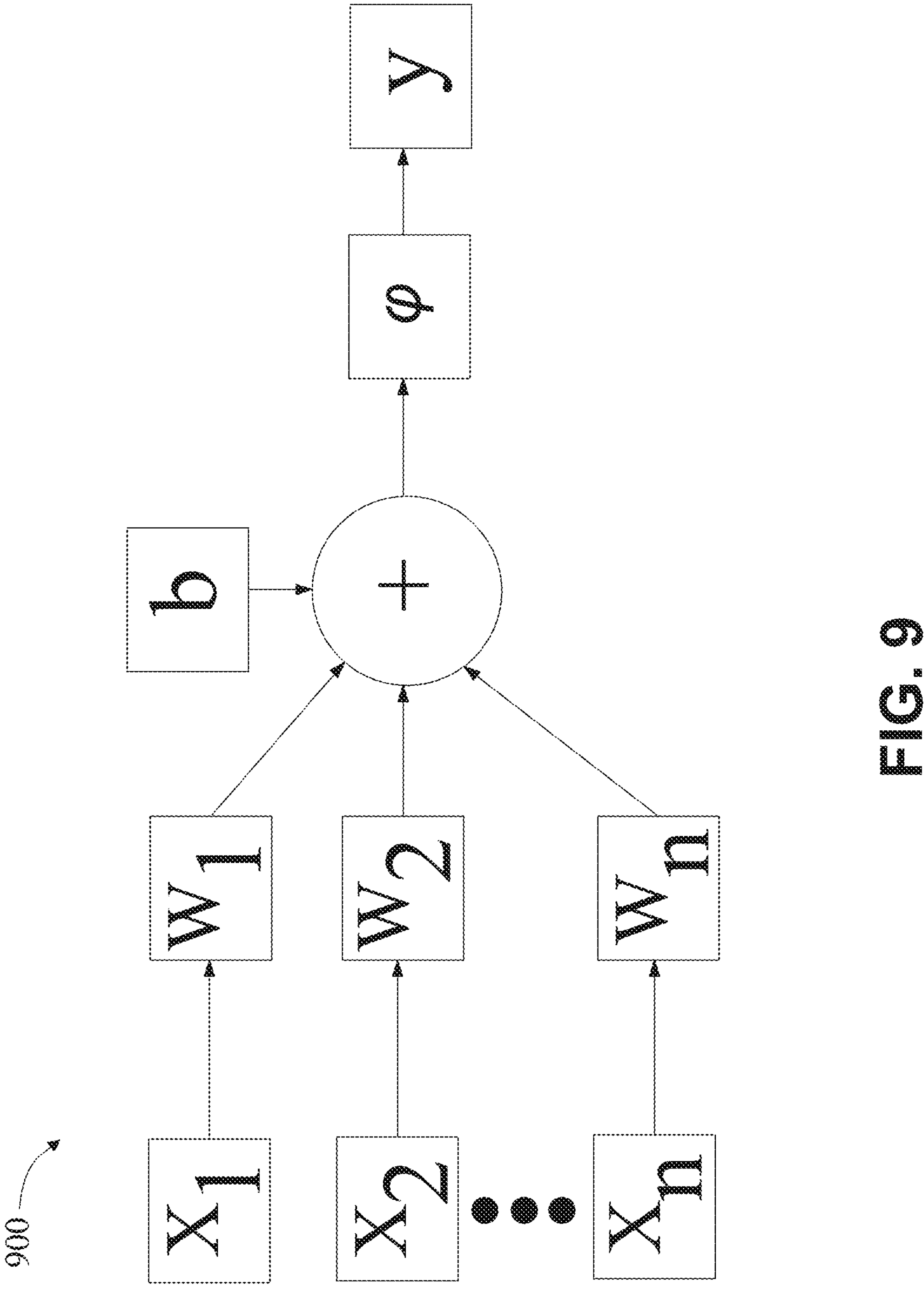
FIG. 9 is a schematic diagram of an exemplary embodiment of a neural network node.

Referring now to FIG. 9, an exemplary embodiment of a node 900 of a neural network is illustrated. A node may include, without limitation a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as f(x)=x*sigmoid (x), a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs x; that may be used as activation functions. As a non-limiting and illustrative example, node may perform a weighted sum of inputs using weights w; that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figures 10A, 10B:
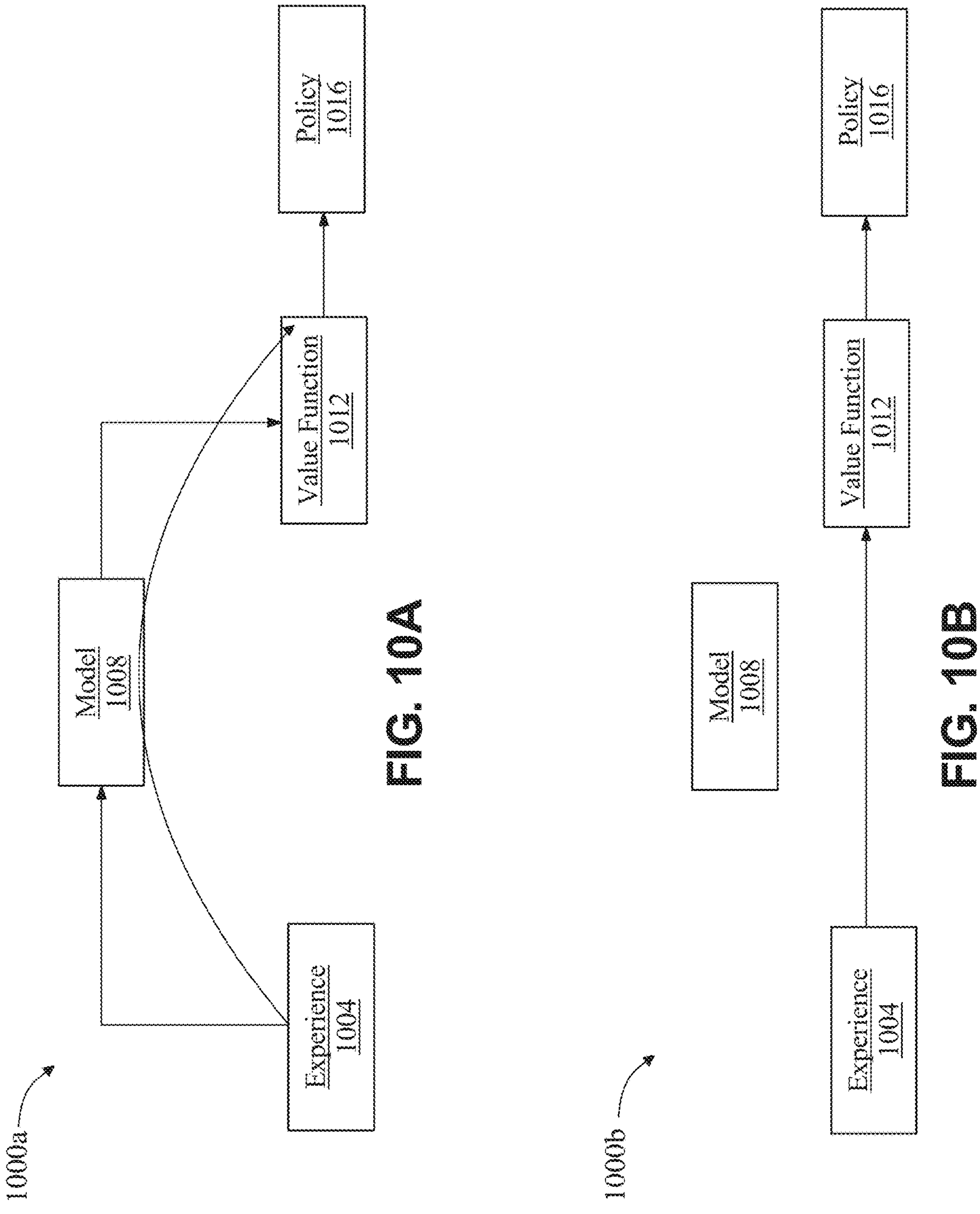
FIG. 10A is a block diagram illustrating an exemplary model-based framework.
FIG. 10B is a block diagram illustrating an exemplary model-free framework.

Now referring to FIG. 10A, a block diagram illustrating an exemplary model-based framework 1000*a* is shown. A model-based framework in reinforcement learning involves learning and/or using a model 1008 of the environment to improve decision-making. In an embodiment, the model 1008 may describe how the environment behaves, for example, by capturing the dynamics of state transitions and/or rewards. In an embodiment, experience 1004 may inform the building or generation of model 1008. In an embodiment, model 1008 may be used for planning which may include simulating potential future states and outcomes, which may further determine optimal courses of action that lead to the most favorable long-term outcome. This process may inform a value function 1012, which estimates the long-term reward for each state. In an embodiment, planning may aid in refining value function 1012 and guide decision-making. These iterations may inform a policy 1016, that may be updated based on iterations of model 1008.

Now referring to FIG. 10B a block diagram illustrating an exemplary model-free framework is shown. A model-free framework in reinforcement learning may involve learning a policy directly from experience 1004 without relying on an explicit model 1008 of the environment. In an embodiment, experience 1004 may consist of state-action-reward tuples, which are collected through direct interaction with the environment. This experience 1004 may be used to estimate the expected reward for each state-action pair, without the need to construct a model 1008 of state transitions or rewards.

In an embodiment, the value function 1012 may be learned directly from experience 1004, estimating the expected cumulative reward for each state (or state-action pair in the case of Q-learning). The value function 1012 may be refined iteratively as more experience is gathered, using algorithms such as temporal difference learning or Monte Carlo methods. The policy 1016 may then be updated based on the learned value function 1012, selecting actions that maximize the expected long-term reward.

In a model-free framework, planning may not be explicitly used, as the agent learns from the accumulated experience without simulating future outcomes. The value function 1012 and policy 1016 may evolve through continuous interactions with the environment, with the agent adjusting its behavior based on the feedback received. This approach may allow for learning an effective policy in environments where a model of the dynamics is difficult to obtain or unnecessary.

Figure 11:
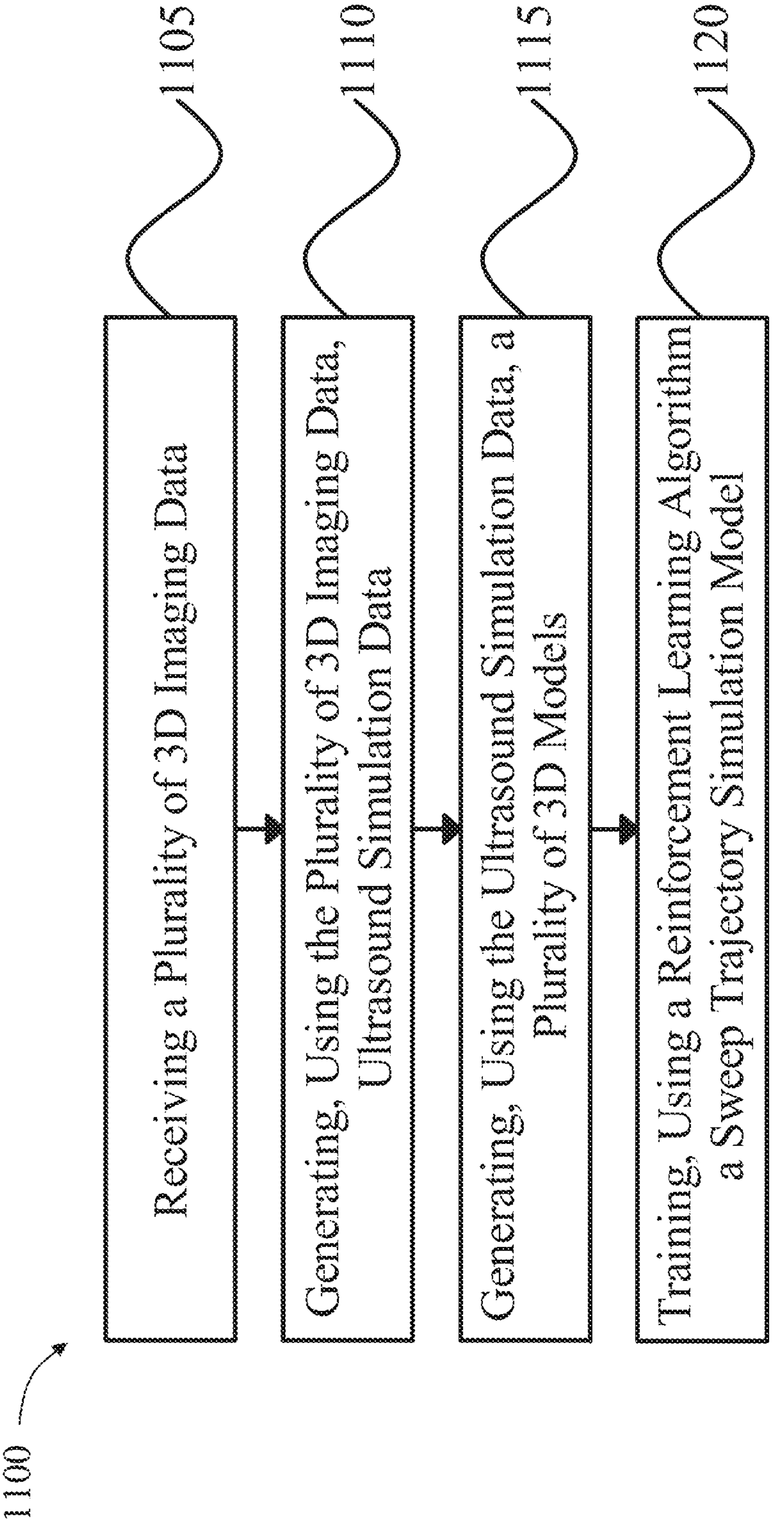
FIG. 11 is a flow diagram depicting an exemplary embodiment of a method of sweep trajectory simulation.

Now referring to FIG. 11, an exemplary method 1100 for sweep trajectory simulation is illustrated. Method 1100 may include a step 1105 of receiving a plurality of 3D imaging data. This may be implemented, without limitation, as referenced in FIGS. 1-9. Method 1100 may include a step 1110 of generating, using the plurality of 3D imaging data, ultrasound simulation data. In an embodiment, the ultrasound simulation data may include ultrasound data and probe position data. In an embodiment, probe position data may include a position and orientation of the ultrasound probe in relation to at least a 3D model of the plurality of 3D models, and one or more movements of the ultrasound probe over time, wherein each position and orientation is correlated to a corresponding temporal element. Further, in some embodiments, the temporal element may correspond to a time-step, and at least a processor may continuously update the position and orientation of the ultrasound probe based on real-time inputs. In an embodiment, method 1100 may further include repeatedly updating the position and orientation of the ultrasound probe as a function of the sweep trajectory simulation model and the time-step vector. Further, in some cases, generating ultrasound simulation data may include capturing expert data, which may be used to train the sweep trajectory simulation model using an imitation learning algorithm and the expert data. This may be implemented, without limitation, as referenced in FIGS. 1-9. M method 1100 may include a step 1115 of generating, using ultrasound simulation data, a plurality of 3D models. This may be implemented, without limitation, as referenced in FIGS. 1-9.

In continued reference to FIG. 11, method 1100 may include a step 1120 of training, using a reinforcement learning algorithm, a sweep trajectory simulation model. In an embodiment, the sweep trajectory simulation model may be trained using 3D imaging data, the probe position data, and the plurality of 3D models. Further, the sweep trajectory simulation model may be configured to output a time-step vector relating to the movement of a catheter. In an embodiment, training a sweep trajectory simulation model may include capturing expert data, training the trajectory simulation model using the expert data, simulating, using the sweep trajectory simulation model, one or more movements of the ultrasound probe, and generating image data as a function of the one or more movements of the ultrasound probe. In some cases, the sweep trajectory simulation model may include a neural network, wherein the neural network includes an input layer configured to receive a ser of features related to a position, orientation, and motion trajectory of the ultrasound probe, one or more hidden layers configured to process and transform the set of features, and an output layer configured to generate a prediction of at least a subsequent movement of the ultrasound probe as function of the set of features. Further, in some embodiments, the neural network may include a training module configured to adjust one or more weights of the neural network by comparing the prediction for at least a subsequent movement of the ultrasound probe to an actual probe movement during simulation. Alternatively, and/or additionally, the sweep trajectory simulation model may include a reinforcement learning model, wherein the reinforcement learning model includes a state representation that defines a current position, orientation, and trajectory of the ultrasound probe within a simulation as a function of the plurality of 3D imaging data and real-time inputs from ultrasound simulation data, an action space that represent s a set of possible movements that can be made to the position and orientation of the ultrasound probe during the simulation, a reward function that evaluates a quality metric of one or more movements of the ultrasound probe based on predefined goals, and a policy that governs how the reinforcement learning model selects actions based on a current state, wherein the policy is learned over time by interacting with the simulation and receiving feedback from the reward function. In one or more embodiments, the reinforcement learning model includes a training process, wherein the training process includes iteratively adjusting the policy as a function of the one or more movements of the ultrasound probe, wherein the one or more movements area associated with positive and negative feedback. at least a processor may be configured to train sweep trajectory simulation model using a model-free reinforcement learning framework, wherein the model-free framework includes generating a policy based on trial-and-error interactions with a simulated environment, updating the policy iteratively by observing rewards and state transitions from the simulated environment and adjusting the policy to maximize cumulative rewards, employing an exploration-exploitation strategy to balance exploration of new trajectories and exploitation of known, high-reward trajectories, and using a value function to estimate the expected reward for state-action pairs, and adjusting the policy accordingly. In an embodiment, method 1000 may include training the sweep trajectory simulation model using inverse reinforcement learning, wherein training sweep trajectory simulation model using inverse reinforcement learning includes receiving expert data representing a set of state-action pairs corresponding to optimal sweep trajectories, estimating a reward function based on the expert data, where the reward function defines the desirability of each state-action pair, iteratively refining the reward function by comparing the outcomes of simulated actions with the expert data, using the reward function as a guide, updating the sweep trajectory simulation model by maximizing an expected reward for a trajectory, and evaluating the trained sweep trajectory simulation model by comparing simulated sweep trajectory outputs with expert data. This may be implemented, without limitation, as referenced in FIGS. 1-9.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
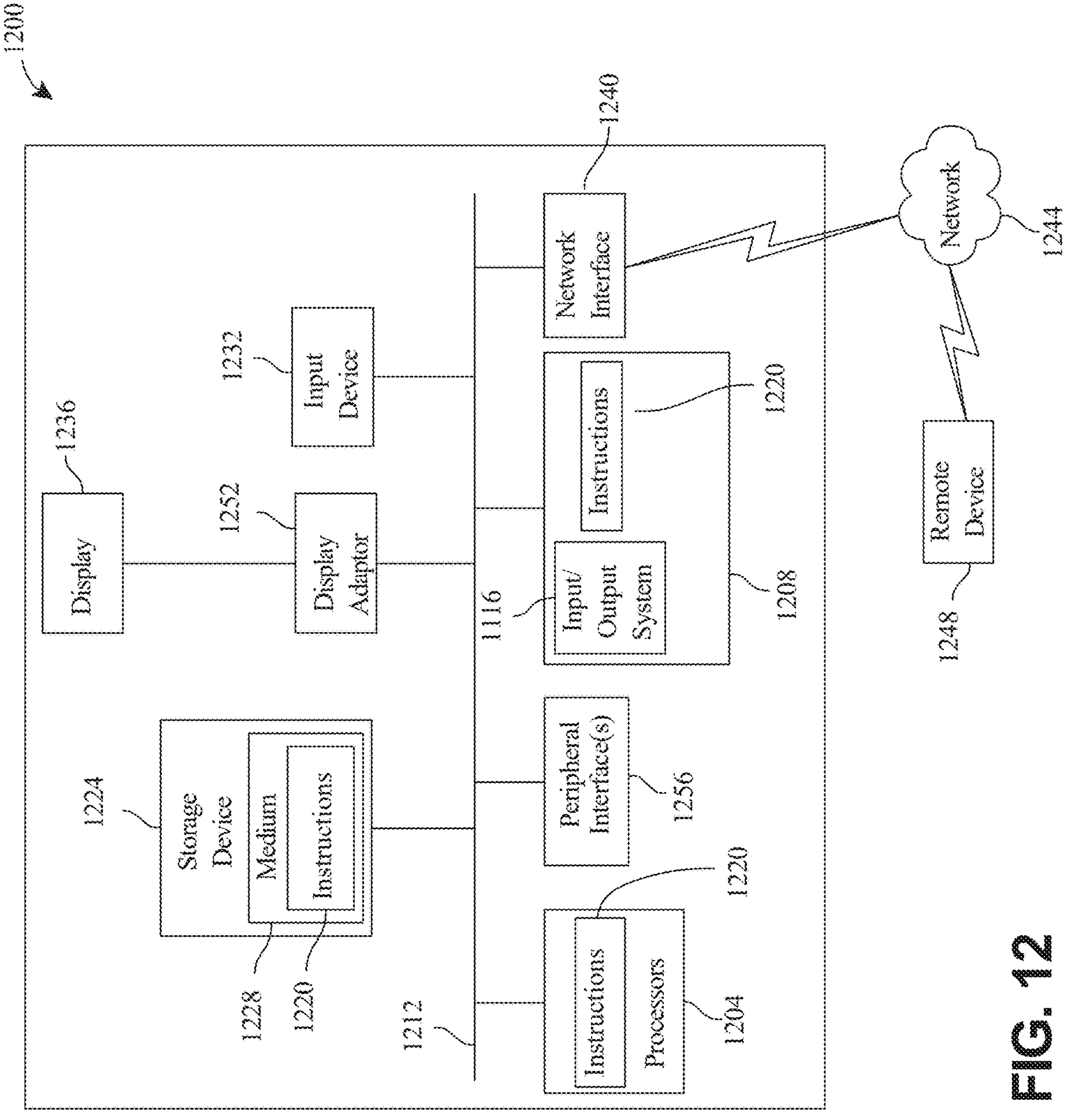
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Processor 1204 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1204 may be organized according to Von Neumann and/or Harvard architecture as a non-limiting example. Processor 1204 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1208 may include various components (e.g., machine-readable media) including, but not limited to, a random-access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display 1236. Examples of a display device include, but are not limited to, a liquid crystal display (LCD), a cathode ray tube (CRT), a plasma display, a light emitting diode (LED) display, and any combinations thereof. Display adapter 1252 and display 1236 may be utilized in combination with processor 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for sweep trajectory simulation, wherein the system comprises:
- at least a processor;
- a memory communicatively connected to the at least processor, wherein the memory contains instructions configuring the at least a processor to:
  - receive a plurality of three-dimensional (3D) imaging data, wherein the plurality of 3D imaging data includes at least a 3D model of a heart;
  - generate, using the plurality of 3D imaging data, ultrasound simulation data, wherein the ultrasound simulation data comprises ultrasound data and probe position data, wherein generating the ultrasound simulation data comprises determining an intracardiac echocardiography (ICE) view based on the 3D model of the heart and including a synthetic ICE frame as a function of the determined ICE view;
  - generate, using the ultrasound simulation data, a plurality of 3D models; and
  - train, using a reinforcement learning algorithm, a sweep trajectory simulation model, wherein:
    - the sweep trajectory simulation model is trained using the 3D imaging data, the probe position data, and the plurality of 3D models; and
    - the sweep trajectory simulation model is configured to output a time-step vector relating to a movement of a catheter; and
- the catheter operatively coupled to the trained sweep trajectory simulation model and configured for use during a procedure, wherein the trained sweep trajectory simulation model is used to control a sweep trajectory of the catheter during the procedure by using the time-step vector as a guiding parameter for controlling real-time movement of the catheter during the procedure.

2. The system of claim 1, wherein the at least a processor is further configured to train the sweep trajectory simulation model using inverse reinforcement learning, wherein training the sweep trajectory simulation model using inverse reinforcement learning comprises:
- receiving expert data representing a set of state-action pairs corresponding to sweep trajectories;
- estimating a reward function based on the expert data, where the reward function defines a desirability of each state-action pair;
- iteratively refining the reward function by comparing outcomes of simulated actions with the expert data, using the reward function as a guide;
- updating the sweep trajectory simulation model by maximizing an expected reward for a trajectory, using reinforcement learning techniques to adjust one or more model parameters; and
- evaluating the trained sweep trajectory simulation model by comparing simulated sweep trajectory outputs with the expert data.

3. The system of claim 1, wherein the at least a processor is further configured to train the sweep trajectory simulation model using a model-free reinforcement learning framework, wherein the model-free framework comprises:
- generating a policy based on trial-and-error interactions with a simulated environment;

updating the policy iteratively by observing rewards and state transitions from the simulated environment and adjusting the policy to maximize cumulative reward;

employing an exploration-exploitation strategy to balance exploration of new trajectories and exploitation of known, high-reward trajectories; and using a value function to estimate an expected reward for state-action pairs and adjust the policy accordingly.

4. The system of claim 1, wherein the probe position data comprises:

a position and orientation of a simulated ultrasound probe in relation to at least a 3D model of the plurality of 3D models; and one or more movements of the simulated ultrasound probe over time, wherein each position and orientation is correlated to a corresponding temporal element.

5. The system of claim 2, wherein the at least a processor is further configured to repeatedly update the position and orientation of the simulated ultrasound probe as a function of the sweep trajectory simulation model and the time-step vector.

6. The system of claim 1, wherein the sweep trajectory simulation model comprises:

a state representation that defines a current position, orientation, and trajectory of an ultrasound probe within a simulation as a function of the plurality of 3D imaging data and real-time inputs from ultrasound simulation data;

an action space that represents a set of possible movements that can be made to the position and orientation of the ultrasound probe during a simulation;

a reward function that evaluates a quality metric of one or more movements of the ultrasound probe based on predefined goals; and a policy that governs how the reinforcement learning model selects actions based on a current state, wherein the policy is learned over time by interacting with the simulation and receiving feedback from the reward function.

7. The system of claim 6, wherein training the sweep trajectory simulation model further comprises administering a training process, wherein:

the training process comprises iteratively adjusting the policy as a function of one or more movements of the ultrasound probe; and the one or more movements are associated with positive and negative feedback.

8. The system of claim 1, wherein:

generating ultrasound simulation data comprises capturing expert data; and training the sweep trajectory simulation model using an imitation learning algorithm using the expert data.

9. The system of claim 8, wherein the sweep trajectory simulation model comprises a neural network, wherein the neural network comprises:

an input layer configured to receive a set of features related to a position, orientation, and motion trajectory of an ultrasound probe;

one or more hidden layers configured to process and transform the set of features; and an output layer configured to generate a prediction for at least a subsequent movement of the ultrasound probe as a function of the set of features.

10. The system of claim 8, wherein training the sweep trajectory simulation model using the imitation learning algorithm using the expert data adjusting one or more weights of the sweep trajectory simulation model by comparing a predicted time-step vector to one or more elements of the expert data.

11. A method for sweep trajectory simulation, wherein the method comprises:

receiving a plurality of three-dimensional (3D) imaging data, wherein the plurality of 3D imaging data includes at least a 3D model of a heart;

generating, using the plurality of 3D imaging data, ultrasound simulation data, wherein the ultrasound simulation data comprises ultrasound data and probe position data, wherein generating the ultrasound simulation data comprises determining an intracardiac echocardiography (ICE) view based on the 3D model of the heart and including a synthetic ICE frame as a function of the determined ICE view;

generating, using the ultrasound simulation data, a plurality of 3D models;

training, using a reinforcement learning algorithm, a sweep trajectory simulation model, wherein:

the sweep trajectory simulation model is trained using the 3D imaging data, the probe position data, and the plurality of 3D models; and the sweep trajectory simulation model is configured to output a time-step vector relating to a movement of a catheter; and using, during a procedure, the catheter operatively coupled to the trained sweep trajectory simulation model, wherein the trained sweep trajectory simulation model is used to control a sweep trajectory of the catheter during the procedure by using the time-step vector as a guiding parameter for controlling real-time movement of the catheter during the procedure.

12. The method of claim 11, further comprising training the sweep trajectory simulation model using inverse reinforcement learning, wherein training the sweep trajectory simulation model using inverse reinforcement learning comprises:

receiving expert data representing a set of state-action pairs corresponding to sweep trajectories;

estimating a reward function based on the expert data, where the reward function defines a desirability of each state-action pair;

iteratively refining the reward function by comparing outcomes of simulated actions with the expert data, using the reward function as a guide;

updating the sweep trajectory simulation model by maximizing an expected reward for a trajectory, using reinforcement learning techniques to adjust one or more model parameters; and evaluating the trained sweep trajectory simulation model by comparing simulated sweep trajectory outputs with the expert data.

13. The method of claim 11, further comprising training the sweep trajectory simulation model using a model-free reinforcement learning framework, wherein the model-free framework comprises:

generating a policy based on trial-and-error interactions with a simulated environment;

updating the policy iteratively by observing rewards and state transitions from the simulated environment and adjusting the policy to maximize cumulative reward;

employing an exploration-exploitation strategy to balance exploration of new trajectories and exploitation of known, high-reward trajectories; and using a value function to estimate an expected reward for state-action pairs and adjusting the policy accordingly.

14. The method of claim 11, wherein the probe position data comprises:

a position and orientation of a simulated ultrasound probe in relation to at least a 3D model of the plurality of 3D models; and one or more movements of the simulated ultrasound probe over time, wherein each position and orientation is correlated to a corresponding temporal element.

15. The method of claim 14, further comprising repeatedly updating the position and orientation of the simulated ultrasound probe as a function of the sweep trajectory simulation model and the time-step vector.

16. The method of claim 11, wherein the sweep trajectory simulation model comprises:

a state representation that defines a current position, orientation, and trajectory of ultrasound probe within a simulation as a function of the plurality of 3D imaging data and real-time inputs from ultrasound simulation data;

an action space that represents a set of possible movements that can be made to the position and orientation of the ultrasound probe during a simulation;

a reward function that evaluates a quality metric of one or more movements of the ultrasound probe based on predefined goals; and a policy that governs how the reinforcement learning model selects actions based on a current state, wherein the policy is learned over time by interacting with the simulation and receiving feedback from the reward function.

17. The method of claim 16, wherein training the sweep trajectory simulation model further comprises administering a training process, wherein:

the training process comprises iteratively adjusting the policy as a function of one or more movements of the ultrasound probe; and the one or more movements are associated with positive and negative feedback.

18. The method of claim 11, wherein:

generating ultrasound simulation data comprises capturing expert data; and training the sweep trajectory simulation model using an imitation learning algorithm using the expert data.

19. The method of claim 18, wherein the sweep trajectory simulation model comprises a neural network, wherein the neural network comprises:

an input layer configured to receive a set of features related to a position, orientation, and motion trajectory of an ultrasound probe;

one or more hidden layers configured to process and transform the set of features; and an output layer configured to generate a prediction for at least a subsequent movement of the ultrasound probe as a function of the set of features.

20. The method of claim 18, wherein training the sweep trajectory simulation model using the imitation learning algorithm using the expert data adjusting one or more weights of the sweep trajectory simulation model by comparing a predicted time-step vector to one or more elements of the expert data.

* * * * *